US005969150A

United States Patent [19]
Donovan et al.

[11] Patent Number: 5,969,150
[45] Date of Patent: *Oct. 19, 1999

[54] IMIDAZOLIUM CATIONS AND PROCESSES FOR THEIR PREPARATION

[75] Inventors: Robert J. Donovan, Center Moriches, N.Y.; Robert J. Morgan, Huntington, W. Va.

[73] Assignee: The Rockefeller University, New York, N.Y.

[ * ] Notice: This patent is subject to a terminal disclaimer.

[21] Appl. No.: 09/124,546

[22] Filed: Jul. 29, 1998

Related U.S. Application Data

[63] Continuation-in-part of application No. 08/673,687, Jun. 25, 1996, Pat. No. 5,874,587.

[51] Int. Cl.[6] ...................... C07D 233/54; C07D 233/00; C07D 345/00; C07H 21/00
[52] U.S. Cl. .................... 548/335.1; 548/300.1; 548/301.7; 540/1; 540/100; 536/22.1; 536/25.32
[58] Field of Search ............................. 548/335.1, 300.1, 548/301.7; 540/1, 100; 536/22.1, 25.32

[56] References Cited

U.S. PATENT DOCUMENTS

| | | | |
|---|---|---|---|
| 5,470,502 | 11/1995 | Hahn et al. | 252/301.35 |
| 5,501,927 | 3/1996 | Imai et al. | 430/78 |
| 5,874,587 | 2/1999 | Donovan et al. | 548/335.1 |

OTHER PUBLICATIONS

Armstrong et al., ACC. Chem. Res., 1966, 29. pp. 123–131.
Ashton et al. (1966) Chem. Eur. J. 31.
Bakthavalam et al., J. Med. Chem., (1991), 34, 3235–3241.
Balzani et al. (1996) Chem. Rev. 96:759–833.
Chao et al. (1996) Nature 380:396–397.
Czarnik, A.W. (1996) Acc. Chem. Res. 29:112–113.
DeWitt et al. (1996) Acc. Chem. Res. 29:114–122.
Ellman, Acc. Chem. Res., 1996, 29 pp. 132–143.
Fabbrizzi et al., Chem. Euro. J., (1966), 2, pp. 75– (et seq.).
Gordon et al., Acc. Chem. Res., 1996, 29, pp. 144–154.
Gutmann et al. (1982) Antimicrob. Agents Chemother. 22:128–136.
Hsieh–Wilson et al. (1966) Acc. Chem. Res. 29:164–170.
Kröhnke, F. (1976) Synthesis, Jan. :1–24.
Kraus et al., Chem Rev., (1996), 96, 523–527.
Marder et al., Science, (1994) 263, pp. 1706–1715.
Rich et al., J. Am. Chem. Soc., (1995), 117, 733–739.
Still, W.C. (1996) Acc. Chem. Res. 29:155–163.
Stoddart et al. (1996) Chem. Eur. J. 2:32.
Tsien, R.Y. (1994) Chem. Eng. News, Jul. 18, pp. 34–44.
Tyagi et al., Nature Biotechnology, 14, pp. 303–308.
Wilchek et al., Analytical Biochemistry, (1988), 171, 1–32.
Yamamoto et al. (1996) J. Am. Chem. Soc. 118:3930–7.
Yitzchaik et al. (1996) Acc. Chem. Res. 29:197–202.

*Primary Examiner*—Ardin H. Marschel
*Assistant Examiner*—Jezia Riley
*Attorney, Agent, or Firm*—Klauber & Jackson

[57] ABSTRACT

The present invention relates to novel imidazolium compounds and improved processes for the preparation of imidazolium cations with one or more imidazolium moieties optionally substituted with the same or different substituents, which are prepared from a reactant with at least one N—C—C—N group, by reacting with with an N-substituted or N,N-disubstituted thioformamide, formamide acetal or thioformamide acetal, in the presence of a halogenating agent. Examples of suitable halogenating agents include but are not limited to thionyl chloride, phosgene, and phosgene derivatives. Reactants containing more than one additional N—C—C—N group may also be used to prepare compounds with two or more imidazolium groups, by the procedures of the present invention. Certain compounds of the invention prepared from reactants with multiple N—C—C—N groups may have both unreacted N—C—C—N moieties and substituted imidazolium groups.

23 Claims, No Drawings

IMIDAZOLIUM CATIONS AND PROCESSES FOR THEIR PREPARATION

CROSS-REFERENCE TO RELATED APPLICATION

This application is a continuation-in-part of application Ser. No. 08/673,687, filed Jun. 25,1996, now U.S. Pat. No. 5,874,587, incorporated herein by reference.

FIELD OF THE INVENTION

This invention relates generally to processes for the preparation of novel imidazolium cations with one or more imidazolium moieties substituted with different substituents, novel fluorescent compounds with multiple imidazolium moieties, and various methods of use for the compounds of the invention.

BACKGROUND OF THE INVENTION

The Vilsmeier-Haack reaction has been an established method for the formylation of aromatic rings. Such formylation, however is applicable mainly to active substrates, such as amines and phenols, and aromatic hydrocarbons which are much more active than benzene such as azulenes and ferrocenes. Typically, $POCl_3$ and dimethylformamide are used as the reactants, although other dialkyl formamides have been used as well. It is also widely used as a method for chlorinating, especially with thionyl chloride, under similar reaction conditions.

As disclosed in co-pending application Ser. No. 08/673,687, now U.S. Pat. No. 5,874,587, novel imidazolium cations are provided and methods for their preparation are described using intermediates containing N—C—C—N moieties which are reacted with N-substituted or N,N-disubstituted formamides in the presence of a halogenating agent. Methods are also disclosed therein for the preparation of compounds with two N—C—C—N moieties both reacted with the formamide reactant. Among other uses, the aforementioned compounds have remarkable color and/or fluorescent properties and have numerous industrial and pharmaceutical utilities.

In further studies of the chemistry, processes for facile synthesis, and utilities of the fluorescent compounds of the aforementioned application, the inventors herein have sought to both control and expand the selection of chemical moieties that may be provided as substituents on these and related compounds as well as provide compounds with one or more N—C—C—N groups which may be substituted as described. It is towards these objectives that the present invention is directed.

OBJECTS OF THE INVENTION

It is an object of the present invention to provide improved processes for the preparation of imidazolium cations with one or more N—C—C—N moieties, and their salts, under favorable conditions in large quantities.

It is a further object of the present invention to provide novel imidazolium cations with two or more N—C—C—N moieties, and salts thereof, which have a variety of utilities.

A still flirther object of the present invention is to provide methods for the preparation of such compounds wherein the substituent, if any, of each N—C—C—N moiety may be selected and controlled.

It is yet a fuirther object of the present invention to provide methods for using the novel imidazolium cations and their salts of the instant invention. These methods include a variety of applications, both industrial and medical, which result from the proper-ties of the aforesaid imidazolium compounds.

Another object of the present invention is to use the process of the invention in combinatorial drug invention systems for labeling and for therapeutic investigation. The instant invention can be used as a linear strategy for combinatorial synthesis.

SUMMARY OF THE INVENTION

The present invention relates to processes for the preparation of imidazolium cations with one or more imidazolium moieties substituted with the same or different substituents. In general, the invention concerns the preparation of a compound of the formula

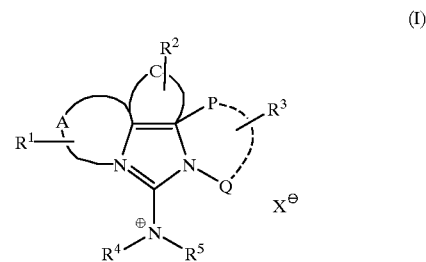

(I)

wherein A is a heteroaromatic ring, which may be optionally substituted by one or more $R^1$ substituents selected from the group consisting of aryl, heteroaryl, alkyl, hydroxy, halo, alkylamino, amino, nitro, cyano or carboxy substituents; P or Q are optional substituents, each independently a substituent selected from the group consisting of aryl, heteroaryl, alkyl, hydroxy, halo, alkylamino, amino, nitro, or carboxy, or P and Q together are a heteroaromatic ring, said P and Q substituents independently or together which may optionally be substituted by one or more $R^3$ substituents selected from the group consisting of aryl, heteroaryl, alkyl, hydroxy, halo, alkylamino, amino, nitro, cyano or carboxy substituents; C is an optional substituent which is an aromatic or heteroaromatic ring, which may optionally be substituted by one or more $R^2$ substituents selected from the group consisting of aryl, heteroaryl, alkyl, hydroxy, halo, alkylamino, amino, nitro, cyano or carboxy substituents;

$R^4$ is hydrogen, an alkyl or aryl group, or together with $R^5$ and the nitrogen atom to which it is attached, form a heterocyclic ring having from 5 to 7 members, which may optionally contain a sulfur, oxygen, silicon, selenium or an additional nitrogen atom, said ring optionally substituted with at least one alkyl group;

$R^5$ is a alkyl or aryl group, or together with $R^4$ and the nitrogen atom to which it is attached, form a heterocyclic ring having from 5 to 7 members, which may optionally contain a sulfur, oxygen, silicon, selenium or an additional nitrogen atom, said ring optionally substituted with at least one alkyl group; and X is an anion, which comprises reaction of a compound of the formula II

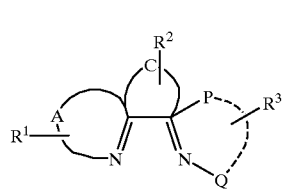

(II)

wherein A, C, P, Q, $R^1$, $R^2$ and $R^3$ are as hereinbefore defined, with a first N-substituted or N,N-disubstituted thioformamide, formamide acetal or thioformamide acetal wherein the N-substituents are referred to as $R^4$ and/or $R^5$, as hereinbefore defined, in a stoichiometric amount, in the presence of a halogenating agent. Examples of suitable halogenating agents include but are not limited to thionyl chloride, phosgene, and phosgene derivatives.

In a further object of the present invention, methods are provided for the preparation of compounds of Formula (I) which have two or more substituted imidazolium groups at positions $R^1$, $R^2$, and $R^3$, which are derived from one or more additional N—C—C—N moieties present on the reactants. Each substitution may be achieved in an independent step utilizing an N-substituted or N,N-disubstituted formnamide, thioformarnide, formnamide acetal or thioformamide acetal, in the presence of a suitable halogenating agent. Preferred halogenating agents for the addition of the formamide may be chosen from thionyl chloride, thionyl bromide, phosphorus oxychloride, phosphorus tribromide, phosphorus truiodide, phosgene, phosphorus thiochloride, thiophosgene, oxalyl chloride, oxalyl bromide, thionyl fluoride, thionyl chloride-fluoride, thionyl iodide, triphosgene, diphosgene, and phosphorus oxychloride. Non-limiting examples of suitable halogenating agents for the addition of the thioformamide, formamide acetal and thioformamide acetal include thionyl chloride, phosgene, and phosgene derivatives, as well as phosgene substitutes such as triphosgene and trichloracetyl chloride.

In another embodiment of the present invention, compounds are provided with a formula as shown in Figure (I) comprising two or more imidazolium groups. Novel compounds are described wherein the imidazolium groups are substituted with different substituents, and wherein compounds with three or more imidazolium groups may have different substituents at each of the imidazolium groups, or some of the N—C—C—N moieties may not be substituted. Furthermore, compounds with four or more substituted or unsubstituted N—C—C—N moieties are described.

It is a further embodiment of the present invention to use in place of the thioformamide reactant other reactants including acetals and thioacetals, to produce similar compounds to those described above.

DETAILED DESCRIPTION OF THE INVENTION

The present invention is directed generally to compounds and processes for the preparation of compounds of the following formula, with the substituents described hereinabove:

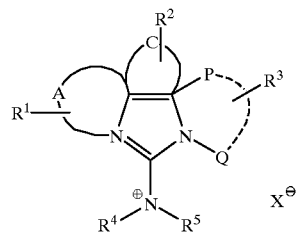

The alkyl groups referred to herein preferably contain from one to about 18 carbon atoms and include lower alkyl groups such as methyl, ethyl, propyl, butyl, pentyl, hexyl, and the corresponding branched-chain isomers thereof, as well as the higher alkyl groups including decyl, undecyl, dodecyl, tetracecyl, hexadecyl, and octadecyl, and their branched-chain isomers. These groups are optionally substituted by one or more halo, hydroxy, amino, nitro, cyano, or alkylamino groups.

As described above, the $R^4$ and $R^5$ groups and the nitrogen atom to which they are attached are derived from reaction of the N—C—C—N-containing reactant with a first N-substituted or an N,N-disubstituted thioformamide (B), formamide acetal (C) or thioformamide acetal (D), as depicted below. Z represents the configuration of the acetal portion of the reactant, indicating a symmetrically or asymmetrically substituted oxygen or sulfur atoms, or a bridged group. One skilled in the art is aware of the multitude of such compounds that may be used in the practice of the present invention, as well as means for preparing such varied reactants. The structures of these compounds are well known in the art. A formamide is shown as (A):

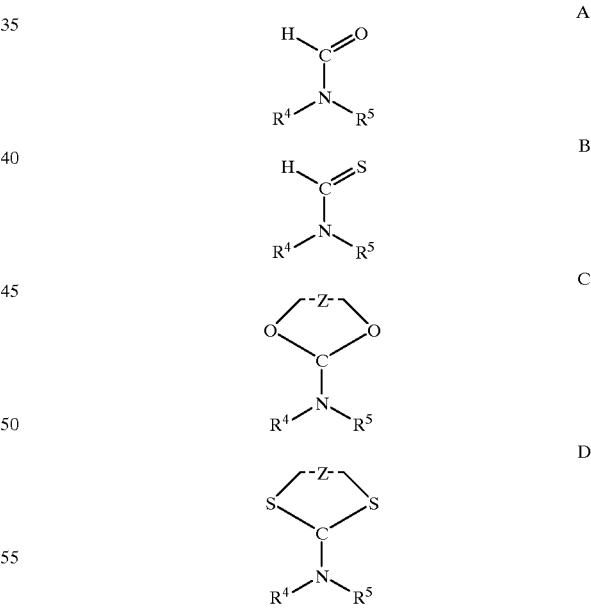

Compounds A–D share a common structure, $C\text{-}N(R^4)(R^5)$ which becomes incorporated into the products of the present invention in forming an imidazolium group from an N—C—C—N moiety. As will be described in more detail below, the selection of the appropriate reactant A–D to provide the desired substituents of the imidazolium product is critical; the selection of whether the reactant is a formamide, thioformamide, formamide acetal or acetal is guided in accordance with the invention herein.

In the instance where $R^4$ and $R^5$, together with the nitrogen atom to which they are attached, form a heterocyclic ring having from 5 to 7 members, which may optionally contain a sulfur, oxygen, silicon, selenium or additional nitrogen atom, such heterocyclic rings are typified by pyrrolyl, imidazolyl, pyrazolyl, pyrrolidinyl, imidazolidinyl, piperdinyl, morpholinyl and piperazinyl groups, which can optionally be substituted by alkyl groups. Especially preferred for use in the present invention are pyrrolidinyl, morpholino and piperazinyl groups.

Where the possibility exists for substitution of a phenyl or aryl ring, the position of the substituents may be ortho, meta, orpara to the point of attachment of the phenyl or aryl ring to the nitrogen of the hydrazine group. Preferably, the substituents are para or meta to the point of attachment, and where more than one is present on the same ring, they are preferably in the para and meta positions.

The halo atoms in the above formula may be fluoro, chloro, bromo or iodo. The lower alkoxy groups contain 1–6, and preferably 1–3, carbon atoms and are illustrated by methoxy, ethoxy, n-propoxy, isopropoxy and the like. The A, C, and P together with Q groups of the compounds of formula I can be selected from a variety of such groups known in the chemical arts. In a preferred embodiment of the present invention, the A group, and P in combination with the Q group, are each a pyridyl ring. Other embodiments are those wherein the A group is a quinolinyl, piperazinyl, or an anthracenyl group, optionally substituted with $R^1$ substitutents. In a further embodiment, one or more of the above-mentioned groups may be a nonaromatic heterocyclic group.

Compounds of the present invention may have two or more N—C—C—N moieties, present by virtue of the substituents at the A, C, and P and/or Q group, with the optional $R^1$, $R^2$, and $R^3$ substituents, respectively. For example, a compound of the present invention may be prepared from a reactant of Formula (II) wherein an additional N—C—C—N moiety is present as comprised by the appropriate $R^1$ and A substituents, or the $R^2$ and C substituents.

The compounds of this invention are salts wherein the $X^-$ anion is derived from an acid, typically one which is biologically and pharmaceutically acceptable. The resultant salts can thus be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic, methanesulfonic and related acids.

The various compounds of the present invention made by the processes disclosed herein may be described based upon (1) the number of N—C—C—N moieties present on the parent (reactant) molecule, (2) the number of those N—C—C—N moieties which are reacted to form substituted imidazolium groups, and (3) the nature of the various substitutions or combinations of substitutions. It is an improvement in the art provided by the present invention to control the reaction at each of the N—C—C—N groups forming the substituted imidazolium groups by using specific reagents at specific concentrations, and thus to the preparation of the desired products. Purification of the products if necessary may be carried out by routine methods known to the skilled artisan.

In the instance wherein the reactant has a single N—C—C—N moiety, and hence forms a singly-substituted imidazolium, the present invention describes a novel process for its preparation using a N-substituted or N,N-disubstituted thioformamide, formamide acetal or thioformamide acetal in the presence of a suitable halogenating agent. Halogenating agents suitable for the addition of the thioformamide, formamide acetal or thioformamide acetal include, but are not limited to, thionyl chloride, phosgene, triphosgene, and a phosgene derivative, such as oxalyl chloride and oxalyl bromide. The selection of the appropriate halogenating agent and conditions for reaction including the reaction temperature will be known to the skilled artisan. Both novel and known compounds may be prepared by this method.

In the instance wherein the compound has two N—C—C—N moieties, and hence may form compounds with either one or two substituted imidazolium groups, it is one object of the present invention to provide a process for preparing compounds with only one of these two reactive groups substituted. Wherein both N—C—C—N groups are substituted, it is a further object of the present invention to provide different substituents at each site. The first substitution may be made by reaction with an equivalent of an N-substituted or an N,N-disubstituted thioformamide, formamide acetal or thioformamide acetal in the presence of a suitable halogenating agent, as described above. Subsequently, the second N—C—C—N moiety may be substituted using an N-substituted or an N,N-disubstituted formamide or thioformamide, formamide acetal or thioformamide acetal, using the appropriate halogenating agent. In another embodiment, the first N—C—C—N moiety may be substituted using a formamide, and the second with a thioformamide, formnamide acetal or thioformnamide acetal. Compounds with two N—C—C—N moieties each substituted with a formamide are described in co-pending application Ser. No. 08/673,687, incorporated herein by reference in its entirety. Thus, where the reactant contains more than one N—C—C—N moiety, it will be appreciated that each of the reactive sites may be the subject of the process disclosed herein by use of different reactants. Numerous "monomer" (containing a single imidazolium ring), "dimer" (containing two imidazolium rings), and "multimeric" (containing more than two imidazolium rings) compounds of this type can be produced by the judicious choice of starting materials and reaction conditions and the sequence by which the different substituents are reacted.

In the instance wherein the compound of the present invention has three N—C—C—N moieties and at least one N—C—C—N moiety is substituted by a formamide or thioformnamide, formamide acetal or thioformamide acetal to produce the corresponding substituted imidazolium, the compound may be prepared by a process of the present invention, and each N—C—C—N moiety may be specifically and individually substituted using the reagents and procedures herein described. Selection of starting materials, formamide, thioformamide, formamide acetal or thioformamnide acetal derivatives and the reaction conditions will be described below in detail.

In the instance wherein the compound of the present invention has four or more N—C—C—N moieties and at least one N—C—C—N moiety is substituted by a formamide or thioformamide, formamide acetal or thioformamide acetal to produce the corresponding substituted imidazolium, the compound may be prepared by a process of the present invention, and each N—C—C—N moiety may be specifically and individually substituted using the reagents and procedures herein described. Selection of starting materials, formamide and thioformamide, formamide acetal or thioformamide acetal derivatives and the reaction conditions will be described below in detail. The invention is not limited by the number of N—C—C—N moieties in the molecule, nor the number of N—C—C—N groups that are reacted to form substituted imidazoliums.

Many suitable starting materials for the compounds of the instant invention are generally known in the art, generally as depicted in the following formula with the substituents as hereinbefore described:

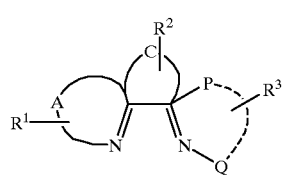

(II)

For instance, Balzani et al., *Chemical Reviews*, 1996, Vol. 96, No. 2, pp. 759–832 and Juris et al., *Coordination Chem. Reviews*, 1988, Vol. 84, pp 85–277, contain references to processes for the preparation of numerous compounds which can be utilized as starting materials for the processes of the instant invention due to their inclusion of the N—C—C—N moiety. Many suitable compounds are also commercially available, for instance, from Aldrich Chemical Co. Other reactants are disclosed in co-pending application Ser. No. 08/673,687, now U.S, Pat. No. 5,874,587, incorporated herein by reference. For example, the following starting materials may be used, classified by the number of N—C—C—N groups. The compounds provided here are by way of example; numerous other compounds with various other or additional substituents are contemplated in the present invention.

Compounds with a single N—C—C—N moiety:2,2'-bipyridine; 4-chloro-2,2'-bipyridine; 4-bromo-2,2'-bipyridine; 4-amino-2,2'-bipyridine; 4-dimethylamino-2,2'-bipyridine; 4-methoxy-2,2'-bipyridine; 4-nitro-2,2'-bipyridine; 4-benzyl-oxy-2,2'-bipyridine; 4-(triethylphosphonio)-2,2'-bipyridine; 6-methyl-2,2'-bipyridine; 6-p-20 styryl-2,2'-bipyridine; 6-p-tolyl-2,2'-bipyridine; 3,3'-dimethyl-2,2'-bipyridine; 3,3-dicarboxyisopropyl-2,2'-bipyridine; 4,4'-dimethyl-2,2'-bipyridine; 4,4'-dichloro-2,2'-bipyridine; 4,4'-dibromo-2,2'-bipyridine; 4,4'-dinitro-2,2'-bipyridine; 4,4'-diamino-2,2'-bipyridine; 4,4'-disulphonate-2,2'-bipyridine; 4,4'-bis(diethylamino)-2,2'-bipyridine; 4,4'-diethoxy-2,2'-bipyridine; 4,4'-diphenoxy-2,2'-bipyridine; 4,4'-dibenzyloxy-2,2'-bipyridine; 4,4'-diphenyl-2,2'-bipyridine; 4,4'-dibenzyl-2,2'-bipyridine; 4,4'-distyryl-2,2'-bipyridine; 4,4'-dicarboxy-2,2'-bipyridine; 4,4'-di-tert-butyl- 2,2'-bipyridine; 4,4'-dinonadecyl-2,2'-bipyridine; 4,4'-distearyl-2,2'-bipyridine;4,4'-dicarboxymethyl-2,2'-bipyridine; N,N'-di(dodecyl)-2,2'-bipyridine-4,4'-dicarboxyamide; N,N'-di(hexadecyl)-2,2'-bipyridine-4,4'-dicarboxyamide; 4,4'-dicarboxyethyl-2,2'-bipyridine; 4,4'-dicarboxyisopyl-2,2'-bipyridine; 4,4'-dicarboxycyclohexyl-2,2'-bipyridine; 4,4'-dicarboxybenzyl-2,2'-bipyridine; 4,4'-dicarboxynapth-2-yl-2,2'-bipyridine; 4,4'-dicarboxynaphthan-1-yl-2,2'-bipyridine; 4,4'-dicarboxydihydrocholesteryl-2,2'-bipyridine; N,N'-di(ethyl)-2,2'-bipyridine-4,4'-dicarboxamide; 4-carboxy-4'-methyl-2,2'-bipyridine; 4-vinyl-4'-methyl-2,2'-bipyridine; 5,5'-dimethyl-2,2'-bipyridine; 5,5'-dicarboxyethyl-2,2'-bipyridine; 5,5'-bisacetoamido-2,2'-bipyridine; 5,5'-dicarboxyisopropyl-2,2'-bipyridine; 6,6'-dimethyl-2,2'-bipyridine; 4,4',5,5'-tetramethyl-2,2'-bipyridine; 2,2'-bipyrazine; protonated 2,2'-bipyrazine; 2,2'-bipyrimidine; 4,4'-dimethyl-2,2'-bipyrimidine; 6,6'-dimethyl-4,4'-bipyrimidine; 3,3'-bipyridazine; 4-methyl-2-(2'-pyridyl)-pyrimidine; 6-methyl-4-(2'-pyridyl)-pyrimidine; 2-(2-aminoethyl)pyridine; o-phenanthroline-5,6-diimine; pyridyl-2-imine; 2-(2-pyridyl)imidazolate anion; 2-(2-pyridyl)imidazole; 2,2'-biimidazote anion; 2,2'-diimidazote anion; 2,2'-biimidazole; 2,2'-dibenzimidazolate dianion; 2,2'-dibenzimidazolate anion; 2,2'-dibenzimidazole; 1-(2-pyridyl)-3,5-dimethylpyrazole; 2-(2'-thiazolyl)-pyridine; 2-(2'-pyridyl)-4-methylthiazole; 4,4'-bithiazole; 2,2-bi-2-thiazoline; 2-p-tolyl-pryidinecarboxaldimine; 2,2'-biquinoline; and 4,4'-dimethyl-2,2'-bipyridine.

Other compounds with a single N—C—C—N moiety useful as reactants for the process of the present invention include compounds such as:7-fluoro-4-carboxymethyl-2-(2-pyridyl)-quinoline; 7-chloro-4-carboxymethyl-2-(2-pyridyl)-quinoline; 7-bromo-4-carboxymethyl-2-(2-pyridyl)-quinoline; 7-iodo-4-carboxymethyl-2-(2-pyridyl)-quinoline; 7-nitro-4-carboxymethyl-2-(2-pyridyl)-quinoline; 7-amino-4-carboxymethyl-2-(2-pyridyl)-quinoline; 7-carboxy-4-carboxymethyl-2-(2-pyridyl)-quinoline; 7-hydroxy-4-carboxymethyl-2-(2-pyridyl)-quinoline; 7-fluoro-4-hydroxymethyl-2-(2-pyridyl)-quinoline; 7-chloro-4-hydroxymethyl-2-(2-pyridyl)-quinoline; 7-bromo-4-hydroxymethyl-2-(2-pyridyl)-quinoline; 7-iodo-4-hydroxymethyl-2-(2-pyridyl)-quinoline; 7-nitro-4-hydroxymethyl-2-(2-pyridyl)-quinoline; 7-amino-4-hydroxymethyl-2-(2-pyridyl)-quinoline; 7-carboxy-4-hydroxymethyl- 2-(2-pyridyl)-quinoline and 7-hydroxy-4-hydroxymethyl-2-(2-pyridyl)-quinoline.

Other reactants in this grouping are compounds with two adjacent N—C—C—N groups of which only one may react with a thioformamide formamide acetal or thidformamide actal in accordance with the present invention. Examples of this type of compound including those with additional reactable N—C—C—N groups, include but are not limited to:4-quinolinecarboxylic acid, 2,2'-(2,6-pyridinyl)bis[6-fluoro-, and 4-quinolinecarboximidamide, 2,2'-(2,6-pyridinyl)bis[N-di-2-pyridinyl-6-quinoxalinyl)]-6-fluoro-.

Compounds with two N—C—C—N moieties:2,3-bis((2-pyridyl)-pyrazine; 7-nitro-2,3-dipyridylquinoxaline; 7-carboxy-2,3-dipyridylquinoxaline; 7,8-dimethyl-2,3-dipyridylquinoxaline; 2,3-pyrazinedicarbonitrile, 5,6-di-2-pyridinyl-; 2,3-pyrazinedicarboxylic acid, 5,6-di-2-pyridinyl-; 2,3-pyrazinediamine, 5,6-di-2-pyridinyl-; 2,3-pyrazinedimethanamine, 5,6-di-2-pyridinyl-; 2,3-pyrazinedicarboxylic acid, 5,6-di-2-pyridinyl-,monomethyl ester; 5H-pyrrolo(3,4-b)pyrazine-5,7(6H)-dione, 2,3-di-2-pyridinyl-; fuiro(3,4-b)pyrazine-5,7-dione, 2,3-di-2-pyridinyl-; 2,3-di-2-pyridylquinoxaline; 2,3,7,8-tetra-2-pyridylpyrazino[2,3-g]quinoxaline; 2,2',3,3'-tetra-2-pyridyl-6,6'-biquinoxaline; 1,2-bis[4-(4'-methyl-2,2'-bipyridinyl)]ethane; 1,5-bis[4-(4'-methyl-2,2'-bipyridinyl)]pentane; 1,4-bis[4-(α-ethyl)-4'-methyl-2,2'-bipyridyl]benzene; 1,12-bis[4,(4'-methyl-2,2'-bipyridyl)dodecane; 2,2',2"-tripyridine; 4'-phenyl-2,2',2"-tripyridine; 4,4',4"-triphenyl-2,2',2"-tripyridine; 2,4,6-tripyridyl-s-triazine; 4-ethynyl-2,2'-bipyridine; 1,12-bis(4-methyl-2,2'-bipyrid-4'-yl)-2-11-diazadodecane; 1,11-bis(4-methyl-2,2'-bipyrid-4'-yl)-6-methyl-2,6, 1 0-triazaundecane; trans-1,2-bis(4'-methyl-2,2'-bipyrid-4-yl)-ethene; 1,4-bis(4-methyl-2,2'-bipyridin-4'-yl)buta-1,3-diene; 1,4-bis(4-methyl-2,2'-bipyridin-4'-yl) buta-1,3-diene; 1,4-bis[2-(2,2'-bipyridin-5-yl)ethenyl]-bicyclo[2.2.2]octane; 1,4-bis(4-methyl-2,2'-bipyridin-4'-yl)-2-cyclohexene-5,6-dicarboxylic acid diethyl ester; 10-bis[[[(2,2'-bipyridinyl-5-yl)carbonyl]6-enzylamino]methyl] anthracene; 1,3,5-tris[[[(2,2'-bipyridyl-5-yl)carbonyl]-benzylamino]methyl]benzene; 1,3,5-tris[[[5-(ethoxycarbonyl-(2,2'-bipyridyl-5-yl)carbonyl)

benzylamino]methyl]phenyl]benzene; 1,3,5-tris[4-[[(2,2'-bipyridyl- 5-ylcarbonyl)benzylamino]methyl]phenyl] benzene-2,2':6,2":6",2"-quaterpyridine; 2,2':4',4":2",2"'-quaterpyridine; 1,2-bis(6'-methyl-2,2'-bipyridin-6-yl)-ethane; 1,4,7,10,13,16-hexakis[(2,2'-bipyridin-6-yl) methyl]-1,4,7,10,13,16-hexaazacyclooctodecane; 2,2':3', 2":6",2"''-quaterpyridine; 2,3-bis(2-pyridyl)pyrazine; 2,5-bis (2-pyridyl)pyrazine; 2,3-bis(2'-pyridyl)quinoxaline; 6,7-dimethyl-2,3-bis(2-pyridyl)quinoxaline; 6,7-dichloro-2,3-bis(2-pyridyl)quinoxaline; 2,3-bis(2'-pyridyl)benzo[g] quinoxaline; 2,2',3,3'-tetra-2-pyridyl-6,6'-biquinoxaline; 2-pyridylacetonitrile; 2,2'-biquinoline; 2,2'-biquinoline-4,4'-dicarboxylic acid; 2,2'-biquinoline-4,4'-dicarboxylic acid dipotassium salt trihydrate; 2,2'-biquinoline-4,4'-dicarboxylic acid disodium salt dihydrate; 2,4-bis(5,6-diphenyl-1,2,4-triazin-3-yl)pyridine; 3-(2-pyridyl)-5,6-di(2-furyl)-1,2,4-triazine-5',5"-disulfonic acid disodium salt; 3-(2-pyridyl)-5,6-diphenyl-1,2,4-triazine; 3-(2-pyridyl)-5,6-diphenyl-1,2,4-triazine-4',4"-disulfonic acid monosodium salt; 2,4,6-tri(2-pyridyl)-s-triazine; 2,3-diaminopyridine; and 1,2,4,5-tetracyanobenzene.

Compounds with three N—C—C—N moieties: 4-quinolinecarboxamide, N-(2,3-di-2-pyridinyl-5-quinoxalinyl)-2-(2-pyridinyl)-; 4-quinolinecarboxamide, N-(2,3-di-2-pyridinyl-6-quinoxalinyl)-6-fluoro-2-(2-pyridinyl)-; 4-quinolinecarboxamide, N-(2,3-di-2-pyridinyl-6-quinoxalinyl)-6-fluoro-2-pyrazinyl-; 4-quinolinecarboxylic acid, 6,6'-[(2,2'-bipyridine)-4,4'-diylbis(carbonylimino)]bis(2-(2-pyridinyl)-.

Compounds with four or more N—C—C—N moieties, as follows. Four: pyrazine(2,3-g)quinoxaline, 2,3,7,8-tetra-2-pyridinyl-; 6,6'-biquinoxaline, 2,2',3,3'-tetra-2-pyridinyl-; 6-quinoxalinecarboxamide, N-(2,3-di-2-pyridinyl-6-quinoxalinyl)-2,3-di-2-pyridinyl-; five: (2,2'-bipyridine)-4, 4'-dicarboxamide, N, N'-bis(2,3-di-2-pyridinyl-6-quinoxalinyl-; six: pyrazinebutanamide, N-(2,3-di-2-pyridinyl-6-quinoxalinyl)-3-((2-[(2,3-di-2-pyridinyl-6-quinoxalinyl)amino]-2-oxoethyl]amino]carbonyl)-γ-oxo-5, 6-di-2-pyridinyl-; eight:1,2,4,5-benzenetetramethanamine, N,N', N", N"'-tetrakis [(2,3-di-2-pyridinyl-6-quinoxalinyl) methyl]-; quinoxaline, 6,6',6''',6''''-[(1,1'-biphenyl]-3,3',4,4'-tetrayltetrakis(oxymethylene)]tetrakis(2,3-di-2-pyridinyl-; ten: [1,1'-biphenyl]- 3,3',4,4'-tetramine, N,N', N", N"'-tetrakis[(2,3-di-2-pyridinyl-6-quinoxalinyl)methyl]-; and sixteen:1,2,4,5-benzenetetramine, N,N'N", N"''-tetrakis[(2,3-di-2-pyridinyl-6-quinoxalinyl)methyl]-. N-substituted and N,N-disubstituted thioformamides, formamide acetals or thioformamide acetals may be used in the processes of the present invention, in order to introduce a substituent on a single N—C—C—N moiety, or in compounds with more than one N—C—C—N moiety, to form different substituents at each site, utilizing a formamide derivative as described above, or a thioformamide, formamide acetal or thioformamide acetal derivative. As described above, this reactant provides the R" and R'" substituents on the imidazolium group of compound (I), one of the R groups being hydrogen when the reactant is N-substituted. Suitable thioformamide derivatives for use in the process of the present invention and for preparing novel compounds are available commercially or may be prepared according to methods known in the art, for example, by Mills (Synthesis 1996:482–483) and Stowell et al. (J. Org. Chem. 54:1212–1213, 1989). Examples of such compounds are provided in the following non-limiting list:
decaborane(8), 1,10-bis(N,N-dimethylmethanethioamide-s)-; carbonocyanidothioic amide, (2,4-dimethoxyphenyl)-; carbonocyanidothioic amide, [2-(1-ethylethyl)phenyl]-; phosphinecarbothioamide, N,N-dimethyl-1,1-diphenyl-; phosphinecarbothioamide, N-methyl-N,1,1-triphenyl-; methanethioamide, n-butyl-; methanethioamide, N-(1,1-methylethyl)-N-2-propenyl-; methanethioamide, N-(1,1-dimethylethyl)-N-methyl-; methanethioamide, N-(1-methylethyl)-N-(trimethylsilyl)-; methanethioamide, N-(1, 1-dimethylethyl)-N-(trimethylsilyl)-; methanethioamide, N-[2,6-bis(1-methylethyl)phenyl]-N-(trimethylsilyl)-; methanethioamide, N-(2,6-dimethylphenyl)-N-(trimethylsilyl)-; methanethioamide, N-phenyl-N-(trimethylsilyl)-; methanethioamide, N-(2,2-dimethylpropyl)-N-(trimethylsilyl)-; methanethioamide, N-(trimethylsilyl)-; methanimidothioic acid, N-(2,2-dimethylpropyl)-; methanethioamide-N,N-d2; methanethioamide-N-d; acetamide, 2-amino-N-methyl-2-thioxo-; methanethioamide, conjugate monoacid; nickel, bis (N,N-diethyl-2-phenyldiazenecarbothioamide-n2,s)-,; methanimidothioic acid, methyl ester; methanethioamide, N-methyl-N-phenyl-; methanethioamide, N-ethyl-N-phenyl-; methanethioamide, N-(2,2-dimethylpropyl)-; methanethioamide, N-[2,6-bis(1-methylethyl)phenyl]-; methanethioamide, N,N-bis(1-methylethyl)-; formamide, N,N-dimethylthio-, compd. with m-dinitrobenzene (1:1); formamide, N,N-dimethylthio-, compd. with iodine (1:1); methanethioamide, N,N-bis(phenylmethyl)-; N,N-dibenzylthioformamide; phosphinecarbothioamide, n, 1,1-triphenyl-,1-oxide; methanethioamide, N-ethyl-; methanethioamide, N,N-diphenyl-; methanethioamide, N-(2,6-dimethylphenyl)-; methanethioamide, N,N-dimethyl-1-(phenylsulfonyl)-; methanethioamide, 1-[(4-chlorophenyl)sulfonyl-N,N-dimethyl-; methanethioamide, N-(phenylmethyl)-; methanethioamide, N-(1-dimethylethyl)-; methanethioamide, N-(1-methylethyl)-; methanethioamide, N-propyl-; formamide, 1-[(p-chlorophenyl)azolthio-; methanethioamide, N-(2-methylpropyl)-; methanethioamide, N-methyl-; diazenecarbothioamide, 2-phenyl-; carbonocyanidothioic amide, dimethyl-; carbamothioic chloride, dimethyl-; phosphinecarbothioamide, 1,1-dicyclohexyl-N-methyl-, 1-oxide; phosphinecarbothioamide, N-methyl-1,1-diphenyl-; formamide, N-methylthio-, compd. with iodomethane (1:1); methanethioamide, N,N-diethyl-; methanethioamide, N,N-dibutyl-; formamide, N,N-diisopropylthio-, compd. with iodomethane (1:1); formamide, N,N-dipropylthio-, compd. with iodomethane (1:1); carbonocyanidothioic amide, methyl-; diazenecarbothioamide, 2-(4-chlorophenyl)-, s-oxide; diazenecarbothioamide, 2-phenyl-, s-oxide; phosphinecarbothioamide, N, 1,1-triphenyl-, 1-sulfide; methanethioamide, monohydrate; carbonocyanidothioic amide, (4-chlorophenyl)-; carbonocyanidothioic amide, (3-chlorophenyl)-; carbonocyanidothioic amide, phenyl-; carbonocyanidothioic amide, (3,4-dichlorophenyl)-; carbonocyanidothioic amide, (2-methylphenyl)-; 3-pyridinecarbothioamide; phosphinecarbothioamide; methanethioamide, N-2-pyridinyl-; methanethioamide, N,N-dimethyl-; methanethioamide, N-phenyl-; carbocyanidothioic amide; and methanethioamide.

Suitable N-substituted and N,N-disubstituted formamides for the present invention include but are not limited to: dimethylformamide, diethyl formamide, dibutyl formamide, 4-formylmorpholine, N-formyl-N-methylaminopyridine, 1-formylpiperazine, 1-formylpiperidine, 1-formylpyrrolidine, N-formylglycine ethyl ester, N-formyl glycine, and N-formylglycine methyl ester.

Suitable formamide acetals for the present invention include but are not limited to: acrolein diacetyl acetal;

acrolein dimethyl acetal; acrolein diacetyl acetal (3,3-diacetoxy-1-propene); N,N-dimethylformamide dibenzyl acetal; N,N-dimethylformamide dibutyl acetal; N,N-dimethylformamide di-tert-butyl acetal; N,N-dimethylformamide diethyl acetal; N,N-dimethylformamide diisopropyl acetal; N,N-dimethylformamide dimethyl acetal; N,N-dimethylformamide dineopentyl acetal; N,N-dimethylformamide dipropyl acetal; and N,N-dimethylformamide ethylene thioacetal.

Suitable thioformamide acetals for the present invention include but are not limited to N,N-dimethylfonmamide direthyl thioacetal; N,N-dhethylformamide diethyl thioacetal; N,N-dinethylformamide dipropyl thioacetal; N,N-dimethylformamide dibutyl thioacetal; N,N-dimethylforramide dipentyl thioacetal; N,N-dimethylformamide dihexyl thioacetal; N,N-dimethylformamide diheptyl thioacetal; N,N-dimethylformamide dibenzyl thioacetal; N,N-dimethylformamide diusopropyl thioacetal; N,N-dimethylformamide dineopenyl thioacetal; and N,N-dimethylformamide ethylene thioacetal Reaction conditions for the instant process vary depending upon the nature of the starting materials, and the presence or absence of a solvent. Typical temperatures range from 0° C. to room temperature. With highly reactive starting materials, a somewhat lower temperature may be desirable, as well as the use of an inert atmosphere, such as a nitrogen or argon, to inhibit side reactions. The reactions described in the present invention have been found to be particularly exothermic. Anhydrous conditions will also help to minimize possible side reactions, especially where m ore than one set of reactive nitrogen atoms are available. Where the various $R^1$, $R^2$ and $R^3$ substituents would allow side reactions, they can be suitably protected, prior to the conduct of the reaction, to avoid such reactions. Furthermore, appropriate dilutions of the reactants may be provided to minimize unwanted side reactions, especially when more than one N—C—C—N moiety is present.

Typical protecting groups useful for such procedures are well-known in the art, and can be removed after isolation of the imidazolium compound. In multi-step synthesis of the present invention, the intermediates may be purified before proceeding to the next step.

When a thioformamide, formamide acetal or thioformamide acetal is used, the halogenating agent is chosen from thionyl chloride, phosgene, triphosgene, and phosgene derivatives. General reaction schemes for preparing the compounds of the present invention are as follows:

Ia. Reaction with a Thioformamide and Thionyl Chloride.

A 50-mL, one neck, round-bottomed flask is equipped with a stirring bar. The flask is charged with 0.50 or 1.0 g of substrate (N—C—C—N compound) and 10 mL of thionyl chloride which is then cooled in an ice water bath to 0° C. for several minutes. To this solution 2 g–4 g (0.0112–0.0224 moles) of dimethyl thioformamide is added. The solution is stirred in a well ventilated hood for an hour and allowed to warm to room temperature. The solution is poured in a 100 mL beaker and the thionyl chloride is allowed to evaporate overnight or is removed using hexane or diethyl ether washes by decanting. $^1$H NMR and $^{13}$C NMR of the adduct shows the desired imidazolium product is formed. The solid fluorescent salt is dissolved in water and sodium perchlorate (NaClO$_4$), ammonium hexafluorophosphate (NH$_4$PF$_6$) or another precipitation salt is subsequently added whereupon the fluorescent adduct precipitates. The solid is then filtered and allowed to air dry. The NMR of the solid is performed to show the purity of the product.

Ib. Reaction with a Formamide Thioacetal and Thionyl Chloride.

The same procedure as described in Ia above is carried out, with 2–4 g dimethylformamide dimethyl acetal use in place of the aforesaid dimethyl thioformamide. All other steps are the same.

Ic. Reaction with a Thioformamide Thioacetal and Thionyl Chloride.

The same procedure as described in Ia above is carried out, with 2–4 g dimethylthioformamide acetal use in place of the aforesaid dimethyl thioformamide. All other steps are the same.

IIa. Reaction with a Thioformamide and Phosgene or Thiophosgene.

A 50-mL, one neck, round-bottomed flask is equipped with a stirring bar. The flask is charged with 0.50 or 1.0 g of substrate and 10 mL of POCl$_3$ or PSCl$_3$ or other unreacting halogenating agents (specifically excluding SOCl$_2$, and phosgene derivatives) which is then cooled in an ice water bath to 0° C. for several minutes. To this solution 2 g–4 g (0.0112–0.0224 moles) of dimethyl thioformamide is added. The solution is stirred in a well ventilated hood for an hour and allowed to warm to room temperature. The solution is poured in a 100 mL beaker and the thionyl chloride is allowed to evaporate overnight or is removed using hexane or diethyl ether washes by decanting. The solid fluorescent salt is dissolved in water and sodium perchlorate (NaClO$_4$) or ammonium hexafluorophosphate (NH4PF$_6$) or other precipitation salt is subsequently added whereupon the fluorescent adduct precipitates. The solid is then filtered and allowed to air dry.

IIb. Reaction with a Formamide Acetal and Phosgene Derivative or Thiophosgene.

The same procedure as described in IIa above is carried out, with 2–4 g dimethylformamide acetal use in place of the aforesaid dimethyl thioformamide. All other steps are the same.

IIc. Reaction with a Thioformamide Acetal and Phosgene or Thiophosgene.

The same procedure as described in hIa above is carried out, with 2–4 g dimethylthioformamide acetal use in place of the aforesaid dimethyl thioformamide. All other steps are the same.

In the following examples, only reaction with thioformamide are depicted, yet these reactions may be performed with a formamide acetal or thioformamide acetal as described in the above examples.

III. Reaction with Excess Thioformaniide and Thionyl Chloride or Phosgene Derivatives.

A 50-mL, one neck, round-bottomed flask is equipped with a stirring bar. The flask is charged with 0.50 or 1.0 g of substrate and 5 mL of dimethyl thioformamide which is then cooled in an ice water bath to 0° C. for several minutes. To this solution an excess of thionyl chloride or phosgene derivatives are added. The solution is stirred in a well ventilated hood for an hour and allowed to warm to room temperature. The solution is poured in a 100 mL beaker and the thionyl chloride is allowed to evaporate overnight or is removed using hexane or diethyl ether washes by decanting. The solid fluorescent salt is dissolved in water and sodium perchlorate (NaClO$_4$) or ammonium hexafluorophosphate (NH4PF$_6$) or other precipitation salt is subsequently added whereupon the fluorescent adduct precipitates. The solid is then filtered and allowed to air dry.

IV. Reaction with a Thioformamide and Excess Thionyl Chloride in Solvent.

A 50-mL, one neck, round-bottomed flask is equipped with a stirring bar. The flask is charged with 0.50 or 1.0 g of substrate and 10 mL of a nonpolar solvent such as toluene, benzene, or hexane, which is then cooled in an ice water bath to 0° C. for several minutes. To this solution 2–4 g (0.0112–0.0224 moles) of dimethyl thioformamide is added. To this solution is added thionyl chloride or phosgene derivatives. The solution is stirred in a well ventilated hood for an hour and allowed to warm to room temperature. The solution is decanted and the remaining solid is washed by using hexane or diethyl ether and decanting. The solid fluorescent salt is dissolved in water and sodium perchlorate ($NaClO_4$) or ammonium hexafluorophosphate ($NH4PF_6$) or other precipitation salt is subsequently added whereupon the fluorescent adduct dissolves and precipitates. The solid is then filtered and allowed to air dry.

The above typical reactions may be employed by the process of the present invention to product various substituted imidazolium compounds. They may be illustrated by the following categories, each with examples described in more detail in the following sections.

When formamides are used in the preparation of compounds of the present invention, a suitable halogenating agent may include, but not be limited to, thionyl chloride, thionyl bromide, phosphorus oxychloride, phosphorus tribromide, phosphorus trichloride, triphosgene, phosphorus triiodide, phosgene, phosphorus thiochloride, thiophosgene, oxalyl chloride, oxalyl bromide and phosphorus oxychloride. Conditions for reaction have been described in co-pending application Ser. No. 08/673,687, now U.S. Pat. No. 5,874,587, as previously described, and incorporated herein by reference.

I. Reaction of a Compound with a Single N—C—C—N Group with a Thioformamide.

The general reaction scheme for the reaction of a N-N disubstituted thioformamide, formamide acetal or thioformamide acetal with the N—C—C—N moiety of the present invention to produce a substituted imidazolium group is illustrated as follows. A N,N-substituted thioformamide, contributing the $R^4$ and $R^5$ substituents to the product, is shown; as described herein this reactant may alternatively be a formamide acetal or thioformamide acetal:

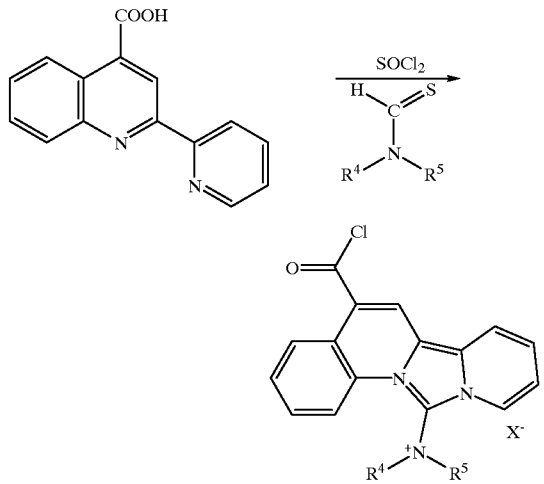

In the above example, the thioformamide provides the -N($R^4$)($R^5$) substituents of the imidazolium group. Various N-subsituted and N,N-disubstituted thioformamides, formamide acetals or thioformamide acetals may be selected for reaction. A representative selection is provided above. Examples of compounds that may be produced by this reaction include both novel and known compounds, such as those disclosed in copending application Ser. No. 08/673, 687 now U.S. Pat. No. 5,874,587,: 12-(dimethylamino-5-carboxy)-pyrido[1',2':3,4]imidazo[1,5-a]quinolin-11-ium perchlorate; 12-(dimethylamino-5-methoxycarbonyl)-pyrido[1',2':3,4]imidazo[1,5-a]quinolin-11-ium perchlorate; 12-(dimethylamino-5-methoxycarbonyl)-pyrido[1',2':3,4] imidazo[1,5-a]quinolin-11-ium perchlorate; 12-(diethylamino-5-carboxy)-pyrido[1',2':3,4]imidazo[1,5-a] quinolin-11-ium perchlorate; 6-(dimethylamino)-dipyrido [1,2-c:2',1'-e]imidazol-5-ium perchlorate; 6-(dimethylamino)-2,10-bis(carboxy)-dipyrido[1,2-c:2',1'-e]imidazol-5-ium perchlorate; 6-(dimethylamino)-2,10-bis (methylcarbonyl)-dipyrido[1,2-c:2',1'-e] imidazol-5-ium perchlorate; 6-(dimethylamino)-6-(2-pyridinyl)-pyrrido[1', 2',:3,4] imidazo [1,5-a]pyrazin-5-ium perchlorate; 6-11-bis (dimethylamino)-bis-pyrido[1',2':3,4]imidazo[1,5-a:5',1'-c] pyrazine-5,10-diium diperchlorate; 12-(dimethylamino)-6-(2-pyridnyl)-pyrido[1',2':3,4]imidazo[1,5-a]quinoxalin-11-ium perchlorate; 6,13-bis-(dimethylamino)-bispyrido[1', 2':3,4]imidazo [1,5-a:5',1'-c]quinoxaline-5,12-diium diperchlorate; 12-(dimethylamino)-6-(2-pyridinyl)-pyrido [1',2':3,4]imidazo[1,5-a]anthacen-11-ium perchlorate; and 6,13-bis(dimethylamino)-bispyrido[1',2':3,4]imidazo[1,5-a:5',1'-c]anthacen-5,10-diium diperchlorate. Novel compounds include but are not limited to pyrido[1',2':3,4] imidazo[1,5-α]quinolin-11-ium,5-carboxy-12-(dimethylamino)-, chloride; pyrido[1',2':3,4]imidazo[1,5-α] quinolin-1-ium,5-carboxy-12-(dimethylamino)-3-fluoro-, chloride; 12H-pyrido[1',2':3,4]imidazo[1,5-α]quinoline-5-carboxylic acid, 3-fluoro-12-[(2-methoxy-2-oxoethyl) imino]-, monohydrochloride; imidazo[1,5-a:3,4-α'] diquinolin-13-ium, 14-(dimethylamino)-, chloride; pyrido [1',2':3,4]imidazo[1,5-α]quinolin-11-ium,5-carboxy-12-(dimethylamino)-3-bromo-, chloride; pyrido[1',2':3,4] imidazo[1,5-α]quinolin-11-ium,5-carboxy-12-(dimethylamino)-3-iodo-, chloride; and pyrido[1',2':3,4] imidazo[1,5-α]quinolin-11-ium,5-carboxy-12-(dimethylamino)-3-(trifluoromethoxy)-, chloride.

The advantages of using a thioformamide, formamide acetal or thioformamide acetal instead of a formamide as described in copending application Ser. No. 08/673,687, now U.S. Pat. No. 5,874,587, is that the addition reaction may be better modulated, especially in the case wherein a single substituent is being added to only one of several substitutable positions on the multiple N—C—C—N reactant (i.e., to produce monomers), in order to achieve a desired product of suitable yield. By performing the reaction under suitably dilute condition, and with suitable halogenating agents, the specificity of the reaction, purity, and yield of the desired product is improved in certain applications.

II. Reaction of Compound with two N—C—C—N Groups with a Single Formamide, Thioformamide, Formamide Acetal or Thioformamide Acetal.

This reaction produces a compound with a single substituted imidazolium group and a N—C—C—N group. An example of this reaction is shown below:

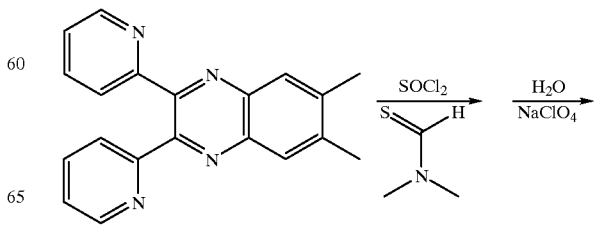

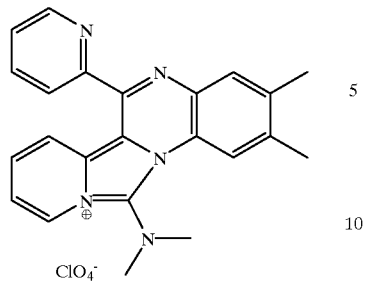

The synthetic route is detailed in the examples below. Conditions must be followed, e.g., reaction at the appropriate dilution, to assure that only one addition occurs per N—C—C—N-containing molecule. Examples of compounds that may be made by this process include the following novel compounds: 6-(dimethylamino)-13-(1-pyrrolidinyl)-dipyrido[2,1-e:2',1'-e']pyrazino[1,2-c:4,3-c] diimidazole-5,10-diium dichloride; 6-(dimethylamino)-13-(1-pyrrolidinyl)-dipyrido[1',2':3,4]imidazo[1,5-a:5',1'-c] quinoxalin-5,12-diium dichloride; 6-(dimethylamino)-13-(1-pyrrolidinyl)-9-methyl-dipyrido[1',2':3,4]imidazo[1,5-a:5c]quinoxalin-5,12-diium dichloride; 6-(dimethylamino)-13-(1-pyrrolidinyl)-9-nitro-dipyrido[1',2':3,4]imidazo[1,5-a:5',1'-c]quinoxalin-5,12-diium dichloride; 6-(dimethylamino)-13-(1-pyrrolidinyl)-9-amino-dipyrido[1',2':3,4]imidazo[1,5-a:5',1'-c]quinoxalin-5,12-diium dichloride; and 6-(dimethylamino)-13-di-(1-pyrrolidinyl)-9-carboxy-dipyrido[1',2':3,4]imidazo[1,5-a:5',1'-c]quinoxalin-5,12-diium dichloride. Purification of the desired product may be obtained by following standard procedures known to the skilled chemist.

III. Reaction of a Compound with Two N—C—C—N Groups Sequentially with Two Different Reactants to Form Two Different Imidazolium Substituents.

An example of this sequential reaction is as follows:

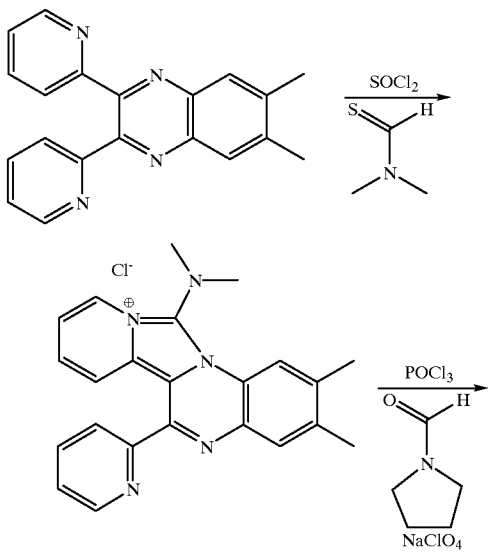

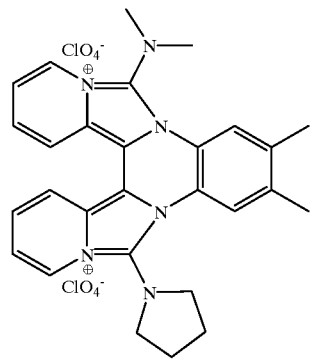

The experimental details may be found in Example 3 below. In the example above, the starting material 7,8-dimethyl-2,3-dipyridylquinoxaline is reacted sequentially, first with dimethyl thioformamide, and subsequently with pyrollidinone formamide, to produce the product with two different imidazolium substituents. The order of reactions may be reversed, i.e., the substituent of the N—C—C—N group provided by the formamide in the above reaction may be added first, followed by the thioformamide (or formamide acetal or thioformamide acetal), contributing the other substituent, each with the corresponding halogenating agent. As described above, and as it has been discovered herein, the extent and specificity of substitution is better controlled by the use of a thioformamide, formamide acetal or thioformamide acetal, and the corresponding halogenating agent, such that in the practice of the invention as pertains to the addition of multiple different substituents to produce a product of the present invention, those additions requiring such better control are preferably performed with the appropriate thioformamide, formamide acetal or thioformamide acetal. It has been found in the above example that it is preferable to use PSCl$_3$ and POCl$_3$, which give higher yields. Examples of the products of this type of reaction include: 6-(4-morpholinyl)-9-methyl-13-(1-pyrrolidinyl)-bispyrido[1',2':3,4]imidazo[1,5-a:5'1'-c]quinoxaline-5,12-diium diperchlorate; 13-(4-morpholinyl)-9-methyl-6-(1-pyrrolidinyl)-bispyrido[1',2':3,4]imidazo[1,5-a:5',1'-c] quinoxaline-5,12-diium diperchlorate; 6-(4-morpholinyl)-9-dimethyl-13-(1-pyrrolidinyl)-bispyrido[1',2':3,4]imidazo[1,5-a:5',1'-c]quinoxaline-5,12-diium diperchlorate; 13-(4-morpholinyl)-9-dimethyl-6-(1-pyrrolidinyl)-bispyrido[1',2':3,4]imidazo[1,5-a:5',1'-c]quinoxaline-5,12-diium diperchlorate; 6-(4-morpholinyl)-9-carboxy-13-(1-pyrrolidinyl)-bispyrido[1',2':3,4]imidazo[1,5-a:5',1'-c] quinoxaline-5,12-diium diperchlorate; 13-(4-morpholinyl)-9-carboxy-6-(1-pyrrolidinyl)-bispyrido[1',2':3,4]imidazo[1,5-a:5',1'-c]quinoxaline-5,12-diium diperchlorate; 6-(4-morpholinyl)-9,10-dicarboxy-13-(1-pyrrolidinyl)-bispyrido[1',2':3,4]imidazo[1,5-a:5',1'-c]quinoxaline-5,12-diium diperchlorate; 13-(4-morpholinyl)-9,10-dicarboxy-6-(1-pyrrolidinyl)-bispyrido[1',2':3,4]imidazo [1,5-a:5',1'-c]quinoxaline-5,12-diium diperchlorate; 6-(4-morpholinyl)-9-methoxycarbonyl-13-(1-pyrrolidinyl)-bispyrido[',2':3,4]imidazo[1,5-a:5',1'-c]quinoxaline-5,12-diium diperchlorate; 13-(4-morpholinyl)-9-methoxycarbonyl-6-(1-pyrrolidinyl)-bispyrido[1',2':3,4]imidazo[1,5-a:5',1'-c]quinoxaline-5,12-diium diperchlorate; 6-(4-morpholinyl)-9-nitro-13-(1-pyrrolidinyl)-bispyrido[1',2':3,4]imidazo[1,5-a:5',1'-c] quinoxaline-5,12-diium diperchlorate; 13-(4-morpholinyl)-9-nitro-6-(1-pyrrolidinyl)-bispyrido[1',2':3,4]imidazo[1,5-a:5',1'-c]quinoxaline-5,12-diium diperchlorate; 6-(4- morpholinyl)-9-amino-13-(1-pyrrolidinyl)-bispyrido[1',2':3, 4]imidazo[1,5-a:5',1'-c]quinoxaline-5,12-diium diperchlorate; 13-(4-morpholinyl)-9-amino-6-(1-pyrrolidinyl)-bispyrido[1',2':3,4]imidazo[1,5-a:5',1 c]quinoxaline-5,12-diium diperchlorate; 6-(4-morpholinyl)-9-hydroxymethane-13-(1-pyrrolidinyl)-bispyrido[1',2':3,4]imidazo[1,5-a:5',1'-c]quinoxaline-5,12-diium diperchlorate; and 13-(4-morpholinyl)-9-hydroxymethane-6-(1-pyrrolidinyl)-bispyrido[1',2':3,4]imidazo[1,5-a:5',1'-c]quinoxaline-5,12-diium diperchlorate.

Further examples of compounds with two different imidazolium substitutions prepared in accordance with the process of the present invention include substituted amino acids, including from single to multiple residues, for example:
alanine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; valine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; leucine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; isoleucine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; phenylalanine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; tryptophan, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; tyrosine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; histidine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; serine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; threonine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; methionine, N-[[13-(4-morpholinyl)-6-(1-pyrrolidinyl)-bispyrido[1',2':3,4]imidazo[1,5-a:5',1'-c]quinoxaline-5,12-diium-9-yl]carbony]-, dichloride; cysteine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl], dichloride; cystine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; aspartic acid, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; glutamic acid, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; asparagine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; glutarniine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; lysine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; arginine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; proline, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; hydroxyproline, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]-, dichloride; glycine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]glycyl-, dichloride; glycine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]glycylglycyl-, dichloride; glycine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]glycylglycylglycyl-, dichloride; glycine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]glycylglycylglycylglycyl-, dichloride; glycine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]glycylglycylglycylglycyl-, dichloride; histidine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]histidinyl-, dichloride; histidine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]histidinylhistidinyl-, dichloride; histidine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]histidinyl-histidinyl-histidinyl-, dichloride; Histidine, N-[[13-(4-morpholinyl)-6-(1-pyrrolidinyl)-bispyrido[1',2':3,4]imidazo[1,5-a:5',1'-c]quinoxaline-5,12-diium-9-yl]carbonyl]histidinyl-histidinyl-histidinyl-histidinyl-, dichloride; and histidine, N-[[13-(4-morpholinyl)-6-(1-pyrrolidinyl)-bispyrido[1',2 ':3,4]imidazo[1,5-a:5',1'-c]quinoxaline-5,12-diium-9-yl]carbonyl]histidinyl-histidinyl-histidinyl-histidinyl-histidinyl, dichloride.

IV. Reaction of a Compound with two N—C—C—N Groups with a Thioformamide to Form a Product with Two Identically- Substituted Imidazolium Groups, as follows:

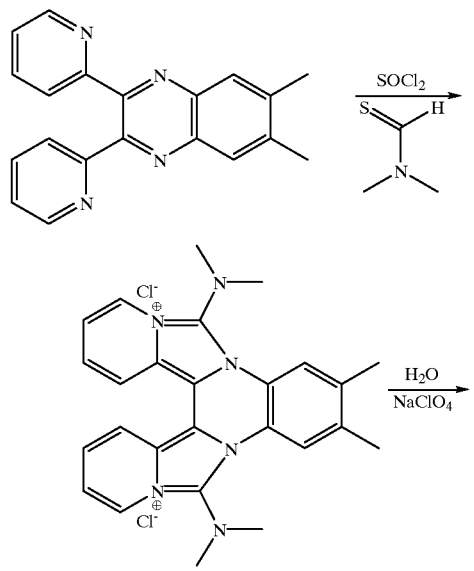

19
-continued

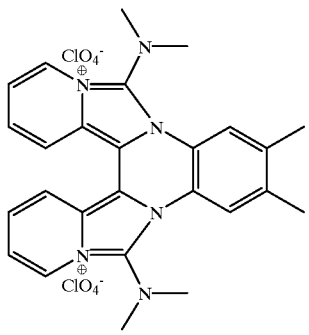

Examples of starting materials for the preparation of these compounds include:
2,3-bis-(2-dipyridyl) pyrazine; 2,3-(2-dipyridyl) quinoxaline; 7-nitro-2,3-(2-dipyridyl)quinoline; 7-methyl-2,3-(2-dipyridyl) quinoline; 7,8-dimethyl-2,3-(2-dipyridyl) quinoline; and 7-carboxy-2,3-(2-dipyridyl)quinoline. Examples of the products include bispyrido[1',2':3,4]imidazo[1,5-a:5',1'-c]quinoxaline-5,12-diium,6, 13-bis(dimethylamino)-9,10-dimethyl-,dichloride; and bispyrido[1',2':3,4]imidazo[1,5-a:5',1'-c]quinoxaline-5,12-diium,9,10-dimethyl-6,13-di-1-pyrrolidinyl-,dichloride.

V. Compounds with Three N—C—C—N Groups may be Derivatized to Form one to three similarly or Differently Substituted Imidazolium Products.

In a like manner as described above, compounds with three N—C—C—N groups such as 4-quinolinecarboxamide, N-(2,3-di-2-pyridinyl-6-quinoxalinyl)-2-(2-pyridinyl)-; 4-quinolinecarboxamide, N-(2,3-di-2-pyridinyl-6-quinoxalinyl)-4-fluoro-2-(2-pyridinyl)-; 4-quinolinecarboxamide, N-(2,3-di-2-pyridinyl-6-quinoxalinyl)-6-fluoro-2-pyrazinyl; and 4-quinolinecarboxylic acid, 6,6'-[(2,2'-bipyridine)-4,4'-diylbis(carbonylimino)]bis[2-(2-pyridinyl)-may be used as reactants to produce the corresponding imidazolium compounds containing from one to three substituted imidazolium groups. To obtain different substitutents, the starting material may be reacted sequentially with the substituted formamide, thioformamide, formamide acetal or thioformamide acetal. Examples of products include: bispyrido[1',2':3,4]imidazo[1,5-a:5',1'-c]quinoxaline-5,12-diium,6, 13-bis(dimethylamino)-9-[((12-(dimethylamino)pyrido[1',2':3,4]imidazo[1,5-α]quinolin-11-ium-5-yl]carbonyl]amino]-, trichloride; pyrido[1',2':3,4]imidazo[1,5-α]quinoxalin-11-ium, 12-(dimethylamino)-2-[((6-fluoro-2-(2-pyridinyl)-4-quinolinyl]carbonyl]amino]-6-(2-pyridinyl)-, chloride; pyrido[1',2':3,4]imidazo[1,5-α]quinoxalin-11-ium, 12-(dimethylamino)-3-[((12-(dimethylamino)-3-[((12-dimethylamino)-3-fluoropyrido-[1',2':3,4]imidazo[1,5-α]quinolin-11-ium-5-yl]carbonyl]amino]-6-(2-pyridinyl)-, dichloride; pyrido[1',2':3,4]imidazo[1,5-α]quinolin-11-ium, 12-(dimethylamino)-5-[((2,3-di-2-pyridinyl-6-quinoxalinyl)amino]carbonyl]-3-fluoro-, chloride; pyrido[1',2':3,4]imidazo[1,5-α]quinoxalin-11-ium, 12-(dimethylamino)-2-[((12-dimethylamino)-3-fluoropyrido[1',2':3,4]imidazo[1,5-α]quinolin-11-ium-5-yl)carbonyl)amino]-6-(2-pyridinyl)-, dichloride; and bipyrido [1',2':3,4]imidazo[1,5-a:5',1'-c]quinoxaline-95,12-diium, 6,13-bis(dimethylamino)-9-[((12-dimethylamino)-3-fluoropyrido[1',2':3,4]imidazo[1,5-α]quinolin-11-ium-5-yl)carbonyl)amino]-6-(2-pyridinyl)-, trichloride.

VI. Compounds with four or more N—C—C—N groups may be prepared following the same procedures as described above.

Examples with one to four imidazoliums include: 34; 35; 36; 37; and 38, as depicted below.

34
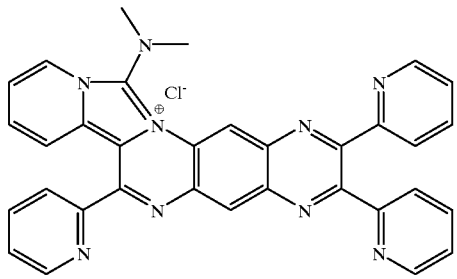

35
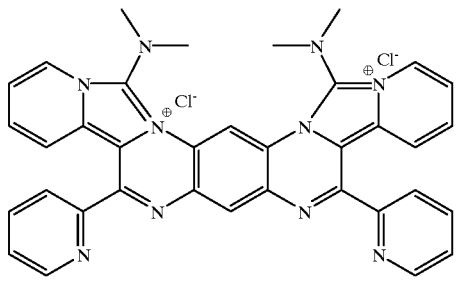

36
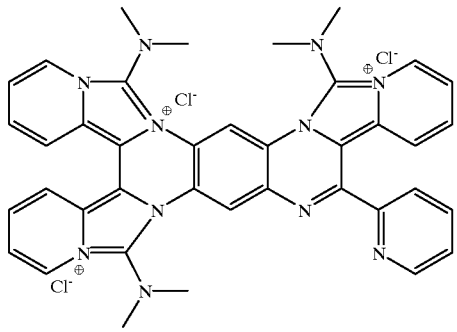

37
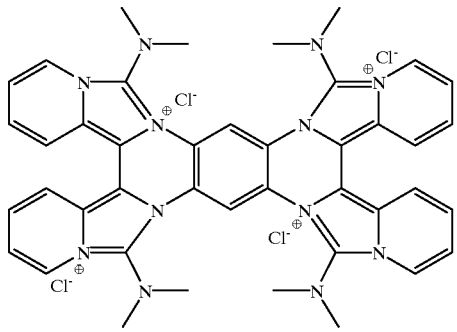

-continued

38

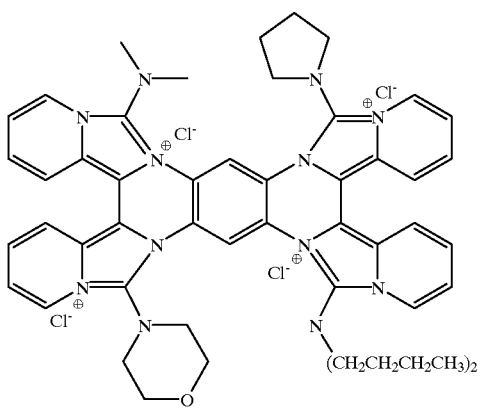

The process of the instant invention provides a convenient and facile process for use in combinatorial synthesis, especially as described by Armstrong et al., *Acc. Chem. Res.*, 1966, 29. pp. 123–131; Ellman, *Acc. Chem. Res.*, 1996, 29 pp. 132–143, and Gordon et al., *Acc. Chem. Res.*, 1996,29, pp. 144–154.

The compounds of the instant invention possess useful properties which make them useful in numerous commercial applications, both industrial and medical, diagnostic and therapeutic. In one embodiment, fluorescent compounds of the present invention may be prepared with covalently attached analytes or other ligands, which thusly labeled are easily detected. Furthermore, the fluorescent and/or color properties of the label may change on interaction of the ligand with an enzyme or receptor. The compounds may thus be used as fluorescent tags coupled to antibodies, receptors, ligands, DNA probes, and the like to localize the specific molecules or to quantitate the presence of the binding partners of the labeled molecules of the present invention, as described in more detail below.

The compounds of the instant invention possess interesting spectroscopic properties, especially visible, ultraviolet, and fluorescent properties, which enable their use in a variety of commercial applications. For instance, the compounds can be used as intensely and brilliantly-colored, "neon"-like dyes in a range of blue, red, green, yellow colors, and especially blue and green colors. The excitation and emission spectra of the compounds may be customized for particular applications, by selection of the appropriate substituents. They can be utilized directly for the dyeing of textiles, and/or may be incorporated into commercially available polymer matrices, in typically, but not limited to, an amount of about 1–3% by weight, based upon the polymer matrix. Preferred apolar polymer matrices are selected from the group consisting of polymethyl methacrylate, polystyrene, polybutadiene-modified polystyrene, polycarbonate, polyvinyl chloride and polyamide, with polymethyl methacrylate and polystyrene matrices being particularly preferred. Other polymer matrices which can also be used include polycondensates based upon urea and formaldehyde or polyamide. Thus, polymer and plastic colorants is one utility of the compounds of the present invention.

It has been noted by the inventors herein that the intensely colored and fluorescent colored compounds of the present invention, when shown or presented to individuals for example in the form of solutions, elicit strong emotional reactions, mostly pleasant, when viewed by certain individuals. As such, the compounds herein may be used in the environment to alter the moods or dispositions of individuals, such as by incorporation into paints or wallpaper, textiles and personally-carried items such as jewelry, to positively affect the perception of an individual or enhance an otherwise unoptimal indoor environment. Increased productivity of individuals exposed to such colors is possible, as well as subliminal communication to change moods, etc., as might be ascribed to the effects of a visual pheromone.

The dyes and pigments of the present invention are prepared in a conventional manner, such as is illustrated in U.S. Pat. No. 5,470,502, whose teachings are herein incorporated by reference. Generally, the fluorescent compound of the instant invention is incorporated into the polymer matrix by extrusion or injection molding. The process of incorporation generally operates at a temperature range of about 150° C. to about 250° C., depending upon the polymer matrix utilized. When polymethyl methacrylate is used, the temperature is generally at a range of about 200° C. to about 240° C.

The novel fluorescent pigments formed by mixing the compounds of the present invention with a polymer matrix are highly suitable for pigmenting waterborne paints, films and inks, and articles made of polyolefins, e.g. polyethylene or polypropylene, and for printing fiber materials, for example, fabrics in polyester or cotton or polyester/cotton blends.

Such fluorescent pigments possess high luminescence and advantageous application properties, for example, high lightfastness and a low migration tendency.

The possession of fluorescent properties further enables the use of the compounds of the instant invention in a variety of medical, pharmaceutical and diagnostic applications. Fluorescent clonal markers can be utilized to elucidate various biological mechanisms, in both animal and plants such as the embryogenesis of an organism, drug binding sites, and drug disposition in the body.

For instance, by attaching a fluorescent compound of the instant invention to a biomolecule such as the end of one arm of a probe sequence of nucleic acids, and a non-fluorescent quench moiety to the end of the other arm of a probe sequence of nucleic acid, the synthesis of specific nucleic acids can be monitored. Similarly, when such fluorescent compounds are used in nucleic acid amplification assays, gene detection is homogeneous and sensitive. Still further, nucleic acid probes containing the fluorescent compounds of the instant invention can be introduced into living cells, thus enabling the origin, movement, and fate of specific mRNAs to be traced. Such methods of attaching fluorescent compounds to such probes have been described in the art, for example in Tyagi et al., *Nature Biotechnology*, 14, pp. 303–308, and T. Stein Chem. Eng. News, Jul. 18, 1994, pp. 34–44. By utilizing the various compounds of the instant invention which emit light of a different frequency, detection of many different targets in the same solution can be identified. For example, a two-dimensional array of immobilized molecular beacons derived from the compounds of the instant invention can be used in a single assay to carry out an extensive survey of an amplified genomic region. Fluorescence is especially useful to probe proteins and DNA.

In similar fashion, the compounds of the instant invention can be utilized as fluorescent tags for any variety of biomolecules to enable the tracking and the disposition of such molecules. Especially important biomolecules which can be tagged by the instant compounds include amino acids, peptides, proteins, β-lactams, oligonucleotides, RNA, DNA, and lipids. The compounds of the instant invention can thus be included in kits to utilize as labeling agents for such biomolecules in various diagnostic and research applications. Methods for utilizing such fluorescent tags for biomolecules are described in, for instance, Rich et al., *J. Am. Chem. Soc.*, (1995), 117, 733–739; Bakthavalam et al., *J. Med. Chem.*, (1991), 34, 3235–3241; Kraus et al., *Chem. Rev.*, (1996), 96, 523–527; and Wilchek et al., *Analytical Biochemistry*, (1988), 171,1–32, whose teachings are herein incorporated by reference, especially those pertinent to the development of biotin related-systems. In the example of proteins and peptides, as described above, various derivatives of single amino acids and peptides containing the imidazolium moiety of the present invention maybe prepared.

A further alternative to labeling already formed biomolecules involves the ab initio synthesis of biomolecules using amino acids which have been reacted in accordance with the process of the instant invention to contain the fluorescent tag within their structure. Typically, a solution of the amino acid, ester thereof or a β-lactam in an anhydrous polar solvent, such as acetonitrile, is reacted with a compound of the instant invention which contains an acyl halide functional group, such as, for instance, the acyl chloride of 2-(2-pyridyl)-4-carboxyquinoline, in the presence of an acid acceptor such as triethylamine. This reaction is typically conducted at temperatures of about 0 to about 20° C. Typical reaction times range from about 1 to 10 hours depending upon the exact nature of the reactants. Non-acid methods of coupling may also be used, such as by the use of carbodiimide. Using this method, one can prepare fluorescent amino acids, both natural and synthetic, which can then be utilized directly in the synthesis of biomolecules to provide fluorescent versions thereof. β-lactams so modified can be used to generate non-naturally occurring amino acids incorporating fluorescence characteristics.

Further, the compounds of the instant invention can be used as fluorescent sensors for transition metals due to the advantages of using a fluorescent tag which can be detected at a very low concentration level. Such usage is described, for instance, by Fabbrizzi et al., *Chem. Euro. J.*, (1996), volume 2, pp. 75 et seq., whose teachings are herein incorporated by reference.

Another utility wherein the instant compounds can be used is in the preparation of non-linear optical polymers or use in conjunction with known non-linear optical polymers. By dissolving a compound of formula I in a polymer, subjecting the polymer to a large electric field at or above its glass transition temperature and cooling the polymer, there is obtained a material with second-order optical non-linearity as described by Marder et al., *Science*, (1994) 263, pp 1706–1715.

The compounds of the instant invention can also be utilized to label various therapeutic agents to enable their disposition in the body. As such, therapy with such labeled therapeutic agents can be closely monitored with respect to target organs and tissues. This is particularly useful in the treatment of various cancers, especially those of a solid tumor type, where localization of the chemo-therapeutic agent is extremely important, and dosage, due to the possibility of side-effects, must be closely monitored. Similarly, the use of such labeled antibiotics can assist in efficacy determinations of penicillins and antibiotics.

The compounds of the invention additionally exhibit antifungal and antimicrobial activity against *Candida albicans*, as well as antiviral activity (HSV). By virtue of such properties, they can be formulated into pharmaceutical compositions, and used to treat infections caused by these invasive organisms.

In a further embodiment of the present invention, polymeric formamide and thioformamides, formamide acetals or thioformamide acetals may be utilized as reactants with the N—C—C—N compounds described herein to produce polymeric, fluorescent compounds with useful properties. For example, polymeric formamide and thioformamides may be used. Furthermore, the N—C—C—N reactants of the present invention may be coupled via their substituents to a polymer, such as polyethylene glycol, forming a polymer comprising numerous N—C—C—N-containing compounds. Reaction of the N—C—C—N compounds in accordance with the present invention forms polymeric products with useful spectral and other properties as described herein.

The present invention may be better understood by reference to the following non-limiting examples, which are provided as exemplary of the invention. The following examples are presented in order to more fully illustrate the preferred embodiments of the invention. They should in no way be construed, however, as limiting the broad scope of the invention.

EXAMPLE 1

Compounds with a single substituted imidazolium moiety may be prepared from the corresponding parent compound with a single N—C—C—N group using the desired N-substituted or N,N-disubstituted thioformamide, formamide acetal or thioformamide acetal derivative, in the presence of the halogenating agents thionyl chloride, phosgene, or a phosgene derivative such as oxalyl chloride or oxalyl bromide.

General reaction conditions are as follows. A 50 mL, one neck, round-bottomed flask is equipped with a stirring bar. The flask is charged with 0.50 g of the substrate (for example, 2,2'-bipyridyl), and 10 mL of thionyl chloride, and is then cooled in an ice water bath for several minutes. To this solution 2 g of the appropriate thioformamide, formamide acetal or thioformamide acetal is added (for example, N,N-dimethyl-methanethioamide). The solution is stirred in a well-ventilated hood for one hour and allowed to warm to room temperature. The solution is then poured into a 100 mL beaker and the thionyl chloride is allowed to evaporate overnight or is removed using diethyl ether washes. After the removal of the thionyl chloride, water is subsequently added and the fluorescent adduct dissolves. To this water solution is added solid ammonium hexafluorophosphate and the fluorescent product immediately precipitates. The solid is then filtered and allowed to air dry.

The following compounds were prepared following the procedure described above.

| Reactant | reactant; Halogenating agent | Product |
|---|---|---|
| 2-(2-pyridyl)-4-carboxyquinoline | N,N-dimethyl-methanethioamide; thionyl chloride | 5-carboxy-12-dimethylamino-pyrido[1',2':3,4]imidazo[1,5-a]quinolin-11-ium perchlorate |
| 4-carboxymethyl-2-(2-pyridyl)-quinoline | N,N-dimethyl-methanethioamide; thionyl chloride | 5-methoxycarbonyl-12-dimethylamino-pyrido[1',2':3,4]imidazo[1,5-a]quinolin-11-ium perchlorate |
| 4-methoxy-2-(2-pyridyl)-4-quinoline | N,N-dimethyl-methanethioamide; thionyl chloride | 5-methoxy-12-dimethylamino-pyrido[1',2':3,4]imidazo[1,5-a]quinolin-11-ium perchlorate |
| 4-chloroethoxycarbonyl-2-(2-pyridyl)-4-quinoline | N,N-dimethyl-methanethioamide; thionyl chloride | 5-chlorethoxycarbonyl-12-dimethylamino-pyrido[1',2':3,4]imidazo[1,5-a]quinolin-11-ium perchlorate |
| (R)-2-(2-(2-pyridyl)-4-carboxyquinoline methylbenzylamide | N,N-dimethyl-methanethioamide; thionyl chloride | 5-carboxy-12-dimethylamino-pyrido[1',2':3,4]imadizo[1,5-a]quinolin-11-ium 5(R)-methylbenzylamide perchlorate |
| (S)-2-(2-(2-pyridyl)-4-carboxyquinoline methylbenzylamide | N,N-dimethyl-methanethioamide; thionyl chloride | 12-dimethylamino-5-carboxy-pyrido[1',2':3,4]imidazo[1,5-a]quinolin-11-ium 5(S)-methylbenzylamide perchlorate |
| 2-(2-pyridyl)-4-carboxyquinoline | N,N-diethyl-methanethioamide; thionyl chloride | 5-carboxy-12-diethylamino-pyrido[1',2':3,4]imidazo[1,5-a]quinolin-11-ium perchlorate |
| 2-(2-pyridyl)-4-carboxyquinoline | N,N-dibutyl-methanethioamide; thionyl chloride | 5-carboxy-12-dibutylamino-pyrido[1',2':3,4]imidazo[1,5-a]quinolin-11-ium perchlorate |

EXAMPLE 2

Compound with two N—C—C—N groups may be reacted with a desired N-substituted or 5 N,N-substituted thioformamide, formamide acetal or thioformamide acetal to derivatize only one of the N—C—C—N groups, forming compounds with one imidazolium group and one underivatized N—C—C—N group. In the examples below, thioformamides are generally used as the reactant; as described above, formamide acetals or thioformamide acetals may also be used for the same purpose. For example:

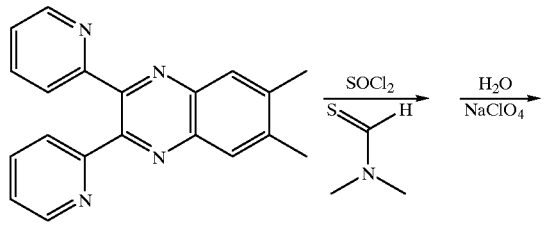

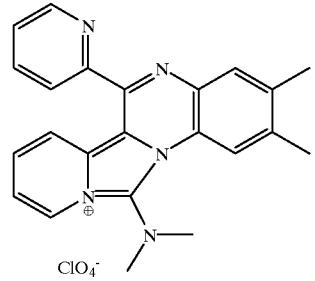

Reaction conditions are as follows. A 250-mL, one neck, round-bottomed flask is equipped with a stirring bar. The flask is charged with 1.0 g of 7,8-dimethyl-2,3-dipyridylquinoxaline ($3.24 \times 10^{-3}$ mole, M.W.=308.3) and 100 mL of toluene which is then cooled in an ice water bath to 0° C. for several minutes. To this solution is added 2 mL of thionyl chloride (SOCl$_2$). To this solution 0.2675 g ($3.0 \times 10^{-3}$ mole, M.W. =89.16) of N,N-dimethylmethanethioamide dissolved in 50 mL of toluene is added dropwise. After the addition of N,N-dirnethylmethanethioamide the solution becomes highly colored and fluorescence is observed. The solution is decanted and the remaining solid is washed with hexane and diethyl ether washes which are also decanted. Water is subsequently added and the fluorescent adduct dissolves. To this water solution is added sodium perchlorate or ammonium hexafluorophosphate and the fluorescent product immediately precipitates. The solid is then filtered and allowed to air dry to give an isolated yield of 1.25 g (90%) (Theory=1.392 g). 12-bis(dimethylamino)-2,3-dimethyl-6-(2-pyridinyl)-pyrido [1',2':3,4]imidazo[1,5-a]qui noxalin-11-ium, perchlorate (M.W.=463.856).

Other compounds with one unsubstituted N—C—C—N and one substituted imidazolium are shown in the table in Example 4.

EXAMPLE 3

Compounds with two N—C—C—N moieties may be reacted in one step with excess thioformamide, formamide acetal or thioformamide acetal to produce compounds with two identically substituted imidazolium groups, or reaction may be performed in two two sequential steps with two different N-substituted or N,N-disubstituted formamides or thioformamides, formamide acetal or thioformamide acetal to produce compounds with two differently substituted imidazolium groups. Examples of the former reactions are as follows:

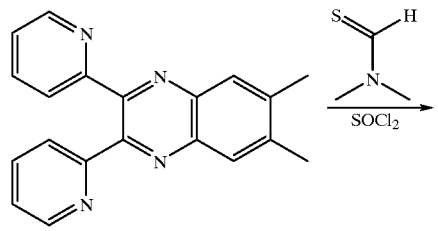

-continued

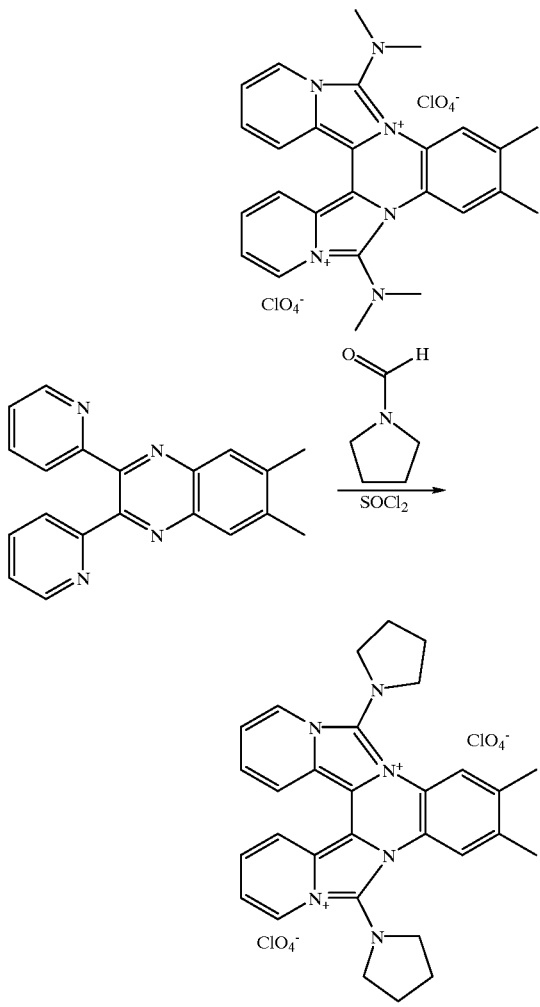

1. A 50-mL, one neck, round-bottomed flask is equipped with a stirring bar. The flask is charged with 1.0 g of 7,8-dimethyl-2,3-dipyridyl quinoxaline ($3.24 \times 10^{-3}$ moles) and 10 mL of thionyl chloride ($SOCl_2$) which is then cooled in an ice water bath to 0° C. for several minutes. To this solution 2 g of N,N dimethyl-methanethioamide (0.0224 moles, M.W.=89.16) is added. After the addition of N,N dimethyl-methanethioamide the solution becomes highly colored and fluorescence is observed. The solution is stirred in a well ventilated hood for an hour and allowed to warm to room temperature. The solution is poured in a 100 mL beaker and the thionyl chloride is allowed to evaporate overnight or is removed using hexane and diethyl ether washes which are decanted. After the removal of the thionyl chloride, water is subsequently added and the fluorescent adduct dissolves. To this water solution is added ammonium hexafluorophosphate and the fluorescent product immediately precipitates. The solid is then filtered and allowed to air dry to give 1.706 g (85%) (Theory=2.007 g) isolated yield 6,13-bis(dimethylamino)-9,10-dimethyl-bispyrido[1',2':3,4] imidazo[1,5-a:5',1'-c]quinoxalin-5,12-diium diperchlorate. In this reaction another 0.1606 g (8.0%) can be obtained by evaporating the thionyl chloride and washing solvents.

2. A 50-mL, one neck, round-bottomed flask is equipped with a stirring bar. The flask is charged with 1.0 g of 7,8-dimethyl-2,3-dipyridyl quinoxaline and 10 mL of thionyl chloride which is then cooled in an ice water bath to 0° C. for several minutes. To this solution 4 mL (4 g) of pyrollidine formamide is added. The solution is stirred in a well ventilated hood for an hour and allowed to warm to room temperature. The solution is poured in a 100 mL beaker and the thionyl chloride is allowed to evaporate overnight or is removed using hexane or diethyl ether washes by decanting. The solid fluorescent salt is dissolved in water and sodium perchlorate ($NaClO_4$) or ammonium hexafluorophosphate ($NH_4PF_6$) or other precipitation salt is subsequently added and the fluorescent adduct dissolves and precipitates. The solid is then filtered and allowed to air dry. $^1H$ NMR and $^{13}C$ NMR of the adduct shows the desired imidazolium product is formed. The NMR of the solid showed that the desired fully substituted product 6,13-di-(1-pyrrolidinyl)-9,10-dimethyl-dipyrido[1',2':3,4]imidazo [1,5-a:5',1'-c]quinoxalin 5,12-diium diperchlorate was obtained pure. [Yield: 87%].

The two-step reaction is depicted as follows:

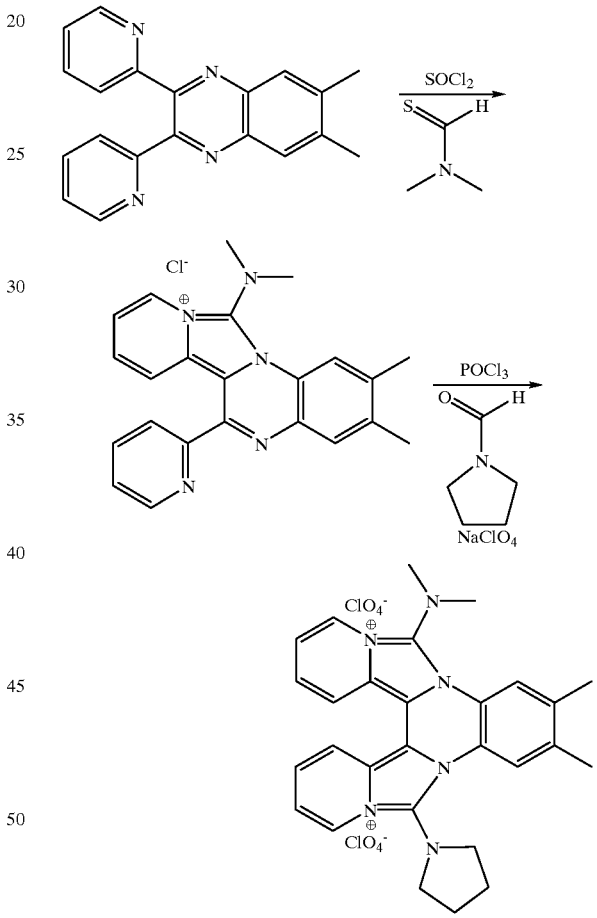

Procedures for carrying out the two-step synthesis are as follows. The order of addition of the two different substitutents may be reversed. The first N—C—C—N is substituted by the following procedure: A 50-mL, one neck, round-bottomed flask is equipped with a stirring bar. The flask is charged with 1.0 g of 7,8-dimethyl-2,3-dipyridyl quinoxaline ($3.24 \times 10^{-3}$ moles) and 110 mL of toluene and 5 mL of thionyl chloride $SOCl_2$ which is then cooled in an ice water bath to 0° C. for several minutes. To this solution 1 equivalent of N,N dimethyl methanethioamide ($3.24 \times 10^{-3}$ moles) dissolved in 20 mL of toluene is added. To this solution 1 equivalent of pyrollidine formamide ($3.24 \times 10^{-3}$ moles) which was dissolved in 20 mL of toluene is added. The solution is then allowed to evaporate overnight under a safety hood. The $^1$H and $^{13}$C NMR showed that this mixed dimer product was formed.

After purification of the singly-substituted intermediate, the second reactant (pyrrolide formamide) is added following steps as described herein. This results in the formation of a product with two different imidazolium substitutions.

Example 4

In a further example of the reaction of a compound with two N—C—C—N groups with a reactand to form two identically-substituted imidazolium groups, the following compound may be made using N,N-dimethylformamide dimethyl acetal:

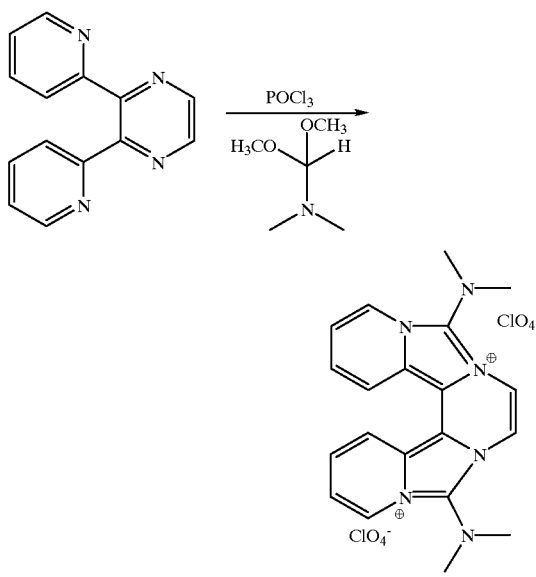

A 25 mL round bottomed flask containing 5 mL of POCl3 is cooled to 0° C. in an ice bath. To the flask is added 0.5 or 1.0 g of 2,3-bis-(2-dipyridyl) pyrazine. To this solution 2 mL of N,N-Dimethylformamide dimethyl acetal. The solution is stirred in a well ventilated hood for an hour and allowed to warm to room temperature. The 5 solution is poured in a 100 mL beaker and the thionyl chloride is allowed to evaporate overnight or is removed using hexane or diethyl ether washes by decanting. The solid fluorescent salt is dissolved in water and sodium perchlorate (NaClO$_4$) generates a precipitate. The solid is then filtered and allowed to air dry. $^1$H NMR and $^{13}$C NMR of the adduct is consistent with that described above.

The reaction also may be carried out using thioformamide and thiophosgene:

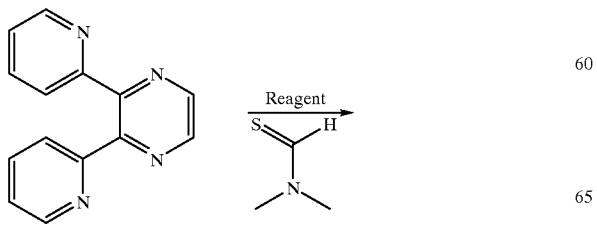

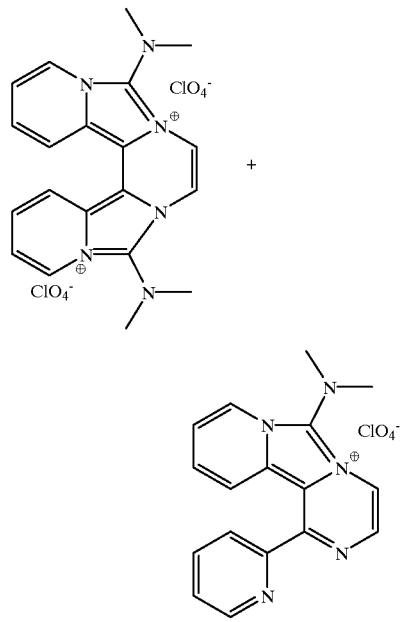

A 25 mL round bottomed flask containing 10 mL of toluene is cooled to 0° C. in an ice bath. To the flask is added 0.5 or 1.0 g of 2,3-bis-(2-dipyridyl) pyrazine. To this solution 5 mL of N,N-dimethyl thioformamide is added. The solution is allowed to cool and 2 mL of thiophosgene is added. The solution instantaneously becomes fluorescent. The solution is stirred in a well ventilated hood for an hour and allowed to warm to room temperature. The solution is decanted and washed with diethyl ether washes. The solid fluorescent salt is dissolved in water and sodium perchlorate (NaClO$_4$) generates a precipitate. The solid is then filtered and allowed to air dry. $^1$H NMR of the adduct is consistent with that obtained previously.

In a further example, the reaction may be carried out using thioformamide and oxalyl chloride:

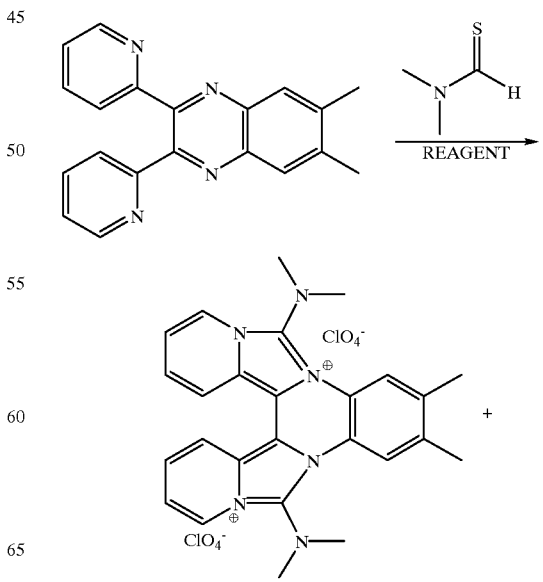

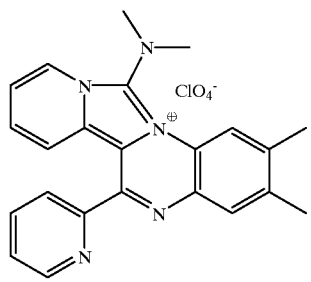

A 25 mL round bottomed flask containing 10 mL of toluene is cooled to 0° C. in an ice bath. To the flask is added 0.5 or 1.0 g of 2,3-bis-(2-dipyridyl)pyrazine. To this solution 5 mL of N,N dimethyl thioformamide. The solution is allowed to cool and approximately 1 mL of oxalyl chloride is added. The solution instantaneously becomes fluorescent. The solution is stirred in a well ventilated hood for an hour and allowed to warm to room temperature. The solution is decanted and washed with diethyl ether washes. The solid fluorescent salt is dissolved in water and sodium perchlorate (NaClO$_4$) generates a precipitate. The solid is then filtered and allowed to air dry. $^1$H NMR of the adduct is consistent with that obtained previously:

Dimer: bispyrido(1',2':3,4)imidazo(1,5-α:5',1'-c)quinoxaline-5-diium,6-13-bis(diamethylamino)-9,10-dimethyl-, diperchlorate.

$^1$H NMR (DMSO, 400 MHz) δ (ppm, multiplicity, integration) 2.60 (s, 6 H), 3.25 (s, 6 H), 3.35 (s, 6 H), 7.35 (t, 2 H), 7.51 (t, 2 H), 8.07 (s, 2 H), 8.46 (d, J=, 2 H), 8.66 (d, J=, 2 H).

$^{13}$C NMR(DMSO, 400 MHz) δ (ppm) 18.89, 38.32, 38.52, 105.93, 117.14, 117.50, 118.43, 119.19, 120.59, 122.05, 125.51, 133.74, 138.59.

DEPT (DMSO, 400 MHz) δ (ppm) 18.89, 38.52, 117.14, 117.50, 118.4, 122.05,

Monomer: pyrido (1',2':3,4)imidazo(1,5-α)quinoxalin-11-ium,12-(dimethylamino)-2,3-dimethyl-6-(2-pyridinyl)-, chloride.

$^1$H NMR (DMSO, 400 MHz) δ (ppm, multiplicity, integration) 2.50 (s, 3 H), 2.60 (s, 3 H), 3.25 (s, 6 H), 7.65 (m, 2 H), 7.80 (dd, 1 H), 8.0 (m, 1 H), 8.04 (s, 1 H), 8.15 (d, J=7.75 Hz, 1 H), 8.22 (dt. J=1.0 Hz, 7.75 Hz, 1 H), 8.55 (s, 1 H), 8.90 (d, J=5.0 Hz, 1 H), 8.96 (m, 1 H).

$^{13}$C NMR (DMSO, 400 MHz) δ (ppm) 20.234, 21.333, 40.003, 111.099, 118.421, 120.490, 121.263, 121.590, 123.341, 123.620, 124.412, 125.064, 125.346, 126.560, 126.919, 127.237, 128.347, 128.638, 130.774, 132.921, 136.812, 138.108, 139.209, 140.713, 140.809, 149.879, 151.718, 155.299.

DEPT (DMSO, 400 MHz) δ (ppm) 20.234, 21.333, 40.003 (CH$_3$), 118.427, 120.495, 121.270, 123.631, 125.346, 126.268, 126.922, 128.353, 130.782, 139.215, 149.884.

Further examples of the synthesis are described below:
N,N-dimethylthioformamide and phosphorous oxychloride (POCl$_3$) and SOCl$_2$: A 50-mL, one neck, round-bottomed flask is equipped with a stirring bar. The flask is charged with 1 g of 7,8-dimethyl-2,3-dipyridylquinoxaline and 10 mL of POCl$_3$ which is then cooled in an ice water bath to 0° C. for several minutes. To this solution 4 mL (4 g, 0.0224 moles) of N,N-dimethylthioformamide is added. This solution does not turn fluorescent and no fluorescent adduct is formed. To this solution 2 mL of thionyl chloride is added and bright orange fluorescence is observed. The solution is stirred in a well ventilated hood for an hour and allowed to warm to room temperature. The solution is washed with hexane or diethyl ether and decanted. The solid fluorescent salt is dissolved in water and sodium perchlorate (NaClO$_4$). The solid is then filtered and allowed to air dry. $^1$H NMR and $^{13}$C NMR of the adduct shows the desired imidazolium product is formed. The NMR of the solid showed that the desired product (fully substituted) was obtained pure.

N,N-dimethylthioformamide and oxalyl chloride: A 50-mL, one neck, round-bottomed flask is equipped with a stirring bar. The flask is charged with 1 g of 7,8-dimethyl-2,3-dipyridylquinoxaline and 5 mL of N,N-dimethyl thioformamide which is then cooled in an ice water bath to 0° C. for several minutes. To this solution 2 mL of oxalyl chloride is added. The solution is stirred in a well ventilated hood for an hour and allowed to warm to room temperature. The solution is washed with hexane or diethyl ether and decanted. The solid fluorescent salt is dissolved in water and sodium perchlorate (NaCl$_4$). The solid is then filtered and allowed to air dry. $^1$H NMR and $^{13}$C NMR of the adduct shows the desired imidazolium product is formed. The NMR of the solid showed that a mixture of monomer and dimer was obtained.

N,N-dimethylthioformamide and thiophosgene: A 50-mL, one neck, round-bottomed flask is equipped with a stirring bar. The flask is charged with 1 g of 7,8-dimethyl-2,3-dipyridylquinoxaline and 10 mL of toluene which is then cooled in an ice water bath to 0° C. for several minutes. To this solution 4 mL (4 g, 0.0224 moles) of dimethyl thioformamide is added. This solution does not turn fluorescent and no fluorescent adduct is formed. To this solution 2 mL of thiophosgene is added and bright orange fluorescence is observed. The solution is stirred in a well ventilated hood for an hour and allowed to warm to room temperature. The solution is washed with hexane or diethyl ether and decanted. The solid fluorescent salt is dissolved in water and sodium perchlorate (NaClO$_4$). The solid is then filtered and allowed to air dry. $^1$H NMR and $^{13}$C NMR of the adduct shows the desired imidazolium product is formed. The NMR of the solid showed that a mixture of monomer and dimer was obtained.

N,N-dimethylthioformamide and triphosgene: A 50-mL, one neck, round-bottomed flask is equipped with a stirring bar. The flask is charged with 1 g of 7,8-dimethyl-2,3-dipyridylquinoxaline and 10 mL of toluene which is then cooled in an ice water bath to 0° C. for several minutes. To this solution 4 mL (4 g, 0.0224 moles) of dimethyl thioformamide is added. To this solution 0.5 g of triphosgene is added and a red precipitate is observed immediately and the solution becomes highly fluorescent. The solution is stirred in a well ventilated hood for an hour and allowed to warm to room temperature. The solution is decanted and washed with hexane or diethyl ether. The solid fluorescent salt is dissolved in water and sodium perchlorate (NaClO$_4$). The solid is then filtered and allowed to air dry. $^1$H NMR and $^{13}$C NMR of the adduct shows the desired imidazolium product is formed. The NMR of the solid showed that a mixture of monomer and dimer was obtained. N,N-dimethylformamide dimethyl acetal and phosphorous oxychloride (POCl$_3$): A 50-mL, one neck, round-bottomed flask is equipped with a stirring bar. The flask is charged with 0.5 g of 7,8-dimethyl-2,3-dipyridylquinoxaline and 5 mL of phosphorous oxychloride which is then cooled in an ice water bath to 0° C. for several minutes. To this solution 4 mL (4 g, 0.0224 moles) of dimethyl thioformamide is added. The solution is stirred in a well ventilated hood for an hour and allowed to warm to room temperature. The solution is washed several times with hexane or diethyl ether and decanted. The solid fluorescent salt is dissolved in water using ice cold water and sodium perchlorate (NaClO$_4$) precipitates the product. The solid is then filtered and allowed to air dry. $^1$H NMR and $^{13}$C NMR of the adduct shows the desired imidazolium product is formed. The $^1$H NMR of the solid showed that a relatively pure dimer was obtained.

Dimethylformamide dimethyl acetal and oxalyl chloride: A 50-mL, one neck, round-bottomed flask is equipped with a stirring bar. The flask is charged with 0.5 g of 7,8-dimethyl-2,3-dipyridylquinoxaline and 10 mL of toluene which is then cooled in an ice water bath to 0° C. for several minutes. To this solution 4 mL (4 g, 0.0224 moles) of dimethyl thioformamide is added. To this solution 1 mL of oxalyl chloride is added and a red precipitate is observed immediately and the solution becomes highly fluorescent. The solution is stirred in a well ventilated hood for an hour and allowed to warm to room temperature. The solution is decanted and washed with hexane or diethyl ether. The solid fluorescent salt is dissolved in water and sodium perchlorate (NaClO$_4$). The solid is then filtered and allowed to air dry. $^1$H NMR and $^{13}$C NMR of the adduct shows the desired imidazolium product is formed. The NMR of the solid showed that a mixture of monomer and dimer was obtained.

Dimethylformamide dimethyl acetal and thiophosgene: A 50-mL, one neck, round-bottomed flask is equipped with a stirring bar. The flask is charged with 1 g of 7,8-dimethyl-2,3-dipyridylquinoxaline and 10 mL of toluene which is then cooled in an ice water bath to 0° C. for several minutes. To this solution 4 mL (4 g, 0.0224 moles) of N,N-dimethyl formamide dimethyl acetal is added. To this solution 1 mL of thiophosgene is added and a red precipitate is observed immediately and the solution becomes highly fluorescent. The solution is stirred in a well ventilated hood for an hour and allowed to warm to room temperature. The solution is decanted and washed with hexane or diethyl ether. The solid fluorescent salt is dissolved in water and sodium perchlorate (NaClO$_4$) precipitates a pure fluorescent product. The solid is then filtered and allowed to air dry. $^1$H NMR and $^{13}$C NMR of the adduct shows the desired imidazolium product is formed. The NMR of the solid showed that a mixture of monomer and dimer was obtained.

Dimethylformamide dimethyl acetal and triphosgene: A 50-mL, one neck, round-bottomed flask is equipped with a stirring bar. The flask is charged with 1 g of 7-nitro-2,3-dipyridylquinoxaline and 10 mL of toluene which is then cooled in an ice water bath to 0° C. for several minutes. To this solution 4 mL (4 g, 0.0224 moles) of N,N-dimethyl formamide dimethyl acetal is added. To this solution 0.5 g of triphosgene is added and a red precipitate is observed immediately and the solution becomes highly fluorescent. The solution is stirred in a well ventilated hood for an hour and allowed to warm to room temperature. The solution is decanted and washed with hexane or diethyl ether. The solid fluorescent salt is dissolved in water and sodium perchlorate (NaClO$_4$). The solid is then filtered and allowed to air dry. $^1$H NMR and $^{13}$C NMR of the adduct shows the desired imidazolium product is formed. The NMR of the solid showed that a mixture of monomer and dimer was obtained.

Dimer:6,13-bis-(dimethylamino)-9-nitro-dipyrido[1',2':3,4]imidazo[1,5-a:5',1'-c]quinoxalin-5,12-diium diperchlorate.

$^1$H NMR (DMSO, 400 MHz) δ (ppm, multiplicity, integration) 3.30 (s, 6 H), 3.31 (s, 6 H), 7.40 (dd, 1 H), 7.44 (dd, 1 H), 7.55 (dd, 1 H), 7.57 (dd, 1 H), 8.45 (d, 2 H), 8.60 (d, 1 H), 8.65 (d, 1 H), 8.70 (m, 2 H), 8.97 (d, 1 H)

$^{13}$C NMR (DMSO, 400 MHz) δ (ppm) 38.91, 105.67, 106.19, 113.87, 116.94, 117.31, 117.61, 119.48, 119.57, 120.30, 122.22, 122.36, 123.16, 123.69, 124.29, 126.02, 126.13, 127.27, 134.77, 135.66, 145.29.

DEPT (DMSO, 400 MHz) δ (ppm) 38.91, 113.88, 117.30, 117.50, 117.58, 117.59, 120.31, 122.19, 122.33, 123.67, 126.00, 126.11.

In a similar manner as above, 7-carboxy-2,3-dipyridyl quinoxaline was reacted with N,N-dimethylthioformamide to produce the corresponding bis(dimethylimidazolium) product:

$^1$H NMR (DMSO, 400 MHz) δ (ppm, multiplicity, integration) 3.23 (s, 6 H), 3.27 (s, 6 H), 7.38 (dd, J=6.95, 14.15 Hz, 1 H), 7.40 (dd, J=6.95, 14.15 Hz, 1 H), 7.51 (d, J=6.95 Hz, 1 H), 7.55 (d, J=6.95 Hz, 1 H), 8.42 (dd, J=1, 7.3 Hz, 2 H), 8.48 (s, 2 H), 8.60 (d, J=7.30, 1 H), 8.64 (d, J=7.30, 1 H), 8.78 (s, 1 H).

$^{13}$C NMR (DMSO,400MHz) δ (ppm) 37.81, 105.73, 106.06, 116.93, 117.16, 117.21, 117.25, 118.89, 119.06, 119.13, 121.54, 121.70, 122.41, 125.43, 129.16, 130.52, 133.74, 134.52, 164.11.

Likewise, the following reaction was preformed:

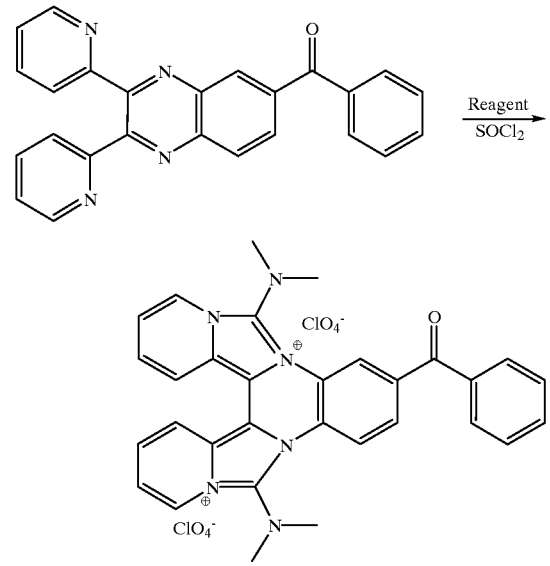

$^1$H NMR (DMSO, 400 MHz) δ (ppm, multiplicity, integration) 3.11 (s, 3 H), 3.12 (s, 3 H), 3.32 (s, 3 H), 3.33 (s, 3 H), 7.43 (dd, 2 H), 7.57 (m, 2 H), 7.70 (dd, 2 H), 7.82 (dd, 1 H), 7.92 (d, 2 H), 8.36 (d, 1 H), 8.47 (d, 2 H), 8.58 (dd, 2 H), 8.68 (bs, 3 H) $^{13}$C NMR (DMSO, 400 MHz) δ (ppm) 40.60, 40.77, 107.65, 108.15, 119.02, 119.28, 119.33, 121.05, 121.17, 121.28, 121.63, 123.71, 123.90, 124.58, 127.33, 127.54, 127.64, 129.50, 130.32, 131.64, 133.99, 135.94, 136.55, 136.76, 137.54, 194.02

DEPT (DMSO, 400 MHz) δ (ppm) 40.60, 40.77, 119.28, 119.55, 119.61, 121.32, 121.90, 123.98, 124.18, 126.27, 127.81, 127.91, 129.77, 130.59, 131.91, 134.26

The following additional reactions were performed as examples of the practice of the present invention.

A 50-mL, one neck, round-bottomed flask is equipped with a stirring bar. The flask is charged with 1.0 g of 7-acetophenone-2,3-dipyridylquinoxaline and 10 mL of thionyl chloride which is then cooled in an ice water bath to 0° C. for several minutes. To this solution 4 mL (4 g) of dimethyl formamide is added. The solution is stirred in a well ventilated hood for an hour and allowed to warm to room temperature. The solution is poured in a 100 mL beaker and the thionyl chloride is allowed to evaporate overnight or is removed using hexane or diethyl ether washes by decanting. The solid fluorescent salt is dissolved in water and sodium perchlorate (NaClO$_4$) or ammonium hexafluorophosphate (NH$_4$PF$_6$) or other precipitation salt is subsequently added and the fluorescent adduct dissolves and precipitates. The solid is then filtered and allowed to air dry. $^1$H NMR and $^{13}$C NMR of the adduct shows the desired midazolium product is formed. The NMR of the solid showed that the desired product (fully substituted) was obtained pure.

A 50-mL, one neck, round-bottomed flask is equipped with a stirring bar. The flask is charged with 1.0 g of 7-acetophenone-2,3-dipyridylquinoxaline and 10 mL of thionyl chloride which is then cooled in an ice water bath to 0° C. for several minutes. To this solution 4 mL (4 g, 0.0224 moles) of dimethyl thioformamide is added. The solution is stirred in a well ventilated hood for an hour and allowed to warm to room temperature. The solution is poured in a 100 mL beaker and the thionyl chloride is allowed to evaporate overnight or is removed using hexane or diethyl ether washes by decanting. The solid fluorescent salt is dissolved in water and sodium perchlorate (NaClO$_4$) or ammonium hexafluorophosphate (NH$_4$PF$_6$) or other precipitation salt is subsequently added and the fluorescent adduct dissolves and precipitates. The solid is then filtered and allowed to air dry. $^1$H NMR and $^{13}$C NMR of the adduct shows the desired imidazolium product is formed. The NMR of the solid showed that the desired product (fully substituted) was obtained pure.

A 50-mL, one neck, round-bottomed flask is equipped with a stirring bar. The flask is charged with 1.0 g of 7-acetophenone-2,3-dipyridylquinoxaline and 10 mL of thionyl chloride which is then cooled in an ice water bath to 0° C. for several minutes. To this solution 4 mL (4 g, 0.0224 moles) of dimethyl thioformamide is added. The solution is stirred in a well ventilated hood for an hour and allowed to warm to room temperature. The solution is poured in a 100 mL beaker and the thionyl chloride is allowed to evaporate overnight or is removed using hexane or diethyl ether washes by decanting. The solid fluorescent salt is dissolved in water and sodium perchlorate (NaCl$_4$) or ammonium hexafluorophosphate (NH$_4$PF$_6$) or other precipitation salt is subsequently added and the fluorescent adduct dissolves and precipitates. The solid is then filtered and allowed to air dry. $^1$H NMR and $^{13}$C NMR of the adduct shows the desired imidazolium product is formed. The NMR of the solid showed that the desired product (fuilly substituted) was obtained pure.

The following compounds were prepared following the above-described procedure. These compounds are novel.

| Reactant | First substitution | Second Substitution | Product |
|---|---|---|---|
| 2,3-bis-(2-dipyridyl)pyrazine | N,N-dimethyl-methanethioamide | none | 6-(dimethylamino)-1-(2-pyridinyl)-pyrido[1',2':3,4]imidazo[1,5-a]pyrazin-5-ium perchlorate |
| 2,3-bis-(2-dipyridyl)quinoxaline | N,N-dimethyl-methanethioamide | N,N-dimethyl-methanethioamide or N,N-dimethylformamide | 6,11-di(dimethylamino)-bispyrido[1',2':3,4]imidazo[1,5-a:5',1'-c]pyrazine-5,10-diium diperchlorate |
| 2,3-bis-(2-dipyridyl)quinoxaline | N,N-dimethyl-methanethioamide | none | 12-(dimethylamino)-6-(2-pyridinyl)-pyrido[1',2':3,4]imidazo[1,5-a]quinoxalin-11-ium perchlorate |
| 2,3-bis-(2-dipyridyl)quinoxaline | N,N-dimethyl-methanethioamide | N,N-dimethyl-methanethioamide or N,N-dimethylformamide | 6,13-bis-(dimethylamino)-Bispyrido[1',2':3,4]imidazo[1,5-a:5',1'-c]quinoxalin-5,12-diium diperchlorate |
| 2,3-bis-(2-dipyridyl)quinoxaline | N,N-dimethyl-methanethioamide | none | 12-(dimethylamino)-6-(2-pyridinyl)-pyrido[1',2':3,4]imidazo[1,5-a]quinoxalin-11-ium perchlorate |
| 2,3-di(2-pyridyl)-1,4,9-triazanapthalene | N,N-dimethyl-methanethioamide | N,N-dimethyl-methanethioamide or N,N-dimethylformamide | beta-azo-6,13-bis-(dimethylamino)-bispyrido[1',2':3,4]imidazo[1,5-a:5',1'-c]quinoxalin-5,12-ium diperchlorate |
| 2,3-di(2-pyridinyl)-1,4,8-triazanaphthalene | N,N-dimethyl-methanethioamide | N,N-dimethyl-methanethioamide or N,N-dimethylformamide | alpha-azo-6,13-bis-(dimethylamino)-bispyrido[1',2':3,4]imidazo[1,5-a:5',1'-c]quinoxalin-5,12-ium diperchlorate |
| 2,3-dipyridinyl-benzo[g]-quinoxaline | N,N-dimethyl-methanethioamide | none | 13-(dimethylamino)-7-(2-pyridinyl)-benzo[g]-pyrido[1',2':3,4]imidazo[1,5-a]quinoxalin-12-ium perchlorate |
| 2,3-dipyridinyl-benzo[g]-quinoxaline | N,N-dimethyl-methanethioamide | N,N-dimethyl-methanethioamide or N,N-dimethylformamide | 7,18-bis(dimethylamino)-benzo[g]bispyrido[1',2':3,4]imidazo[1,5-a:5',1'-c]quinoxaline-6,17-diium bishexafluorophosphate | in water and sodium perchlorate (NaClO$_4$) or ammonium hexafluorophosphate (NH$_4$PF$_6$) or other precipitation salt is subsequently added and the fluorescent adduct dissolves and precipitates. The solid is then filtered and allowed to air dry. $^1$H NMR and $^{13}$C NMR of the adduct shows the desired imidazolium product is formed. The NMR of the solid showed that the desired product (fully substituted) was obtained pure.

EXAMPLE 5

Compounds with three or more N—C—C—N moieties may be reacted in multiple steps with the desired N-substituted or N,N-disubstituted formamides or thioformamides, formamide acetals or thioformamide acetals to produce imidazolium compounds with one, two, or three or more different substituents. In the example of compound with three N—C—C—N groups, by adjusting the number of equivalents of the formamide reactants, it is possible to prepare compounds with two similar substituents and a third different substituent in a two-step process. Using excess formamide or thioformamide, all three N—C—C—N groups may be substituted to form the same substituted imidazolium. The same principles apply to compounds with more than three N—C—C—N groups. Compounds with multiple imidazolium groups, for example up to about 16 or more, may be prepared from starting reactants with multiple N—C—C—N groups, in accordance with the by the procedures described herein. Such multimeric compounds may have from one to all of the N—C—C—N moieties as substituted imidazolium moieties. Polymeric structures with considerably more N—C—C—N groups, similar to dendrimers, also may be prepared.

General procedures for carrying out the one-, two-, or three-step synthesis are as described above. Examples of the reactants with three or more N—C—C—N groups and products with from one to all of the N—C—C—N groups derivatized to form substituted imidazolium groups are also provided above.

EXAMPLE 6

Imidazolium compounds with higher alkyl substituents may be made from the corresponding N—C—C—N containing reactants in accordance with the following procedures:

Preparation of 2,3-bis-(2-pyridyl)6-carboxybutylquinoxaline. To a 10 mL roundbottomed flask, fitted with a magnetic stirring bar, was added 985 mg (3.0 mmol) of 2,3-bis-(2-pyridyl)6-carboxybutylquinoxaline and 121 mg. (1.0 mmol) of 4-dimethylaminopyridine (DMAP) and 3 mL methylene chloride. With stirring was added a 3.6 mL of 1.0 M (3.6 mmol) 1,3-dicyclohexylcarbodiimide (DCC) in methylene chloride in a single portion. After stirring for 5 minutes, 223 mg (3.0 mmol) of 1-butanol was added, and stirring was continued for an additional 12 hours. The thick reaction mixture was filtered (gravity) and the solid (DCU) washed with methylene chloride (2 mL×3) and the methylene chloride removed under reduced pressure on a rotary evaporator. The semi-solid residue was dried in vacuo at 80° C. for 2 hours. Hexane was added and the mixture refluxed for 120 minutes. Any solids were removed by filtration, and the hexane removed under reduced pressure, giving 2a as a colorless semi-solid which slowly crystallized. The crude 2a (1.10 g) was chromatographed on a silica column, packed with chloroform and gradient eluted by addition of ethyl acetate. Removal of the mobile phase gave 2,3-bis-(2-pyridyl)-6-carboxybutylquinoxaline as a pale yellow oil which slowly crystallized into a colorless solid (1.0 g, 86%).

Preparation of 2,3-bis-(2-pyridyl)6-carboxyhexylquinoxaline. To a 10 mL roundbottomed flask, fitted with a magnetic stirring bar, was added 656 mg (2.0 mmol) of 2,3-bis-(2-pyridyl)6-carboxyquinoxaline and 121 mg (1.0 mmol) of DMAP and 4 mL methylene chloride. With stirring was added a 3.6 mL of 1.0 M (3.6 mmol) DCC in methylene chloride in a single portion. After stirring for 5 minutes, 307 mg (3.0 mmol) of 1-hexanol was added, and stirring was continued for an additional 12 hours. The thick reaction mixture was filtered (gravity) and the solid (DCU) washed with methylene chloride (2 mL×3) and the methylene chloride removed under reduced pressure on a rotary evaporator. The semi-solid residue was dried in vaccu at 80° C. for 12 hours.

Preparation of 2,3-bis-(2-pyridyl)6-carboxyoctylquinoxaline. To a 10 mL roundbottomed flask, fitted with a magnetic stirring bar, was added 656 mg (2.0 mmol) of 2,3-bis-(2-pyridyl)-6-carboxyquinoxaline and 121 mg (1.0 mmol) of DMAP and 4 mL methylene chloride. With stirring was added 2.6 mL of 1.0 M (2.6 mmol) DCC in methylene chloride in a single portion. After stirring for 5 minutes, 356 mg (2.0 mmol) of 1-octanol was added, and stirring was continued for an additional 12 hours. The thick reaction mixture was filtered (gravity) and the solid (DCU) washed with methylene chloride (2 mL×3) and the methylene chloride removed under reduced pressure on a rotary evaporator. The crude solid was chromatographed on a silica column which was flushed with one volume of chloroform and the product could be eluted using a chloroform/ethylacetate gradient. Evaporation of the mobile phase, gave product as a light yellow semisolid, which crystallized into a white solid upon trituration and pentane (520 mg, 58%).

Preparation of 2,3-bis-(2-pyridyl)6-carboxydecylquinoxaline. To a 10 mL roundbottomed flask, fitted with a magnetic stirring bar, was added 985 mg (3.0 mmol) of 2,3-bis-(2-pyridyl)6-carboxyquinoxaline and 121 mg (1.0 mmol) of DMAP and 6 mL methylene chloride. With stirring was added 3.6 mL of IM (3.6 mmol) DCC in methylene chloride in a single portion. After stirring for 5 minutes, 475 mg (3.0 mmol) of I-decanol was added, and stirring was continued for an additional 12 hours. The thick reaction mixture was filtered (gravity) and the solid (DCU) washed with methylene chloride (2 mL×3) and the methylene chloride removed under reduced pressure on a rotary evaporator. The semisolid residue was dried in vacuo at 80° C. for 12 hours giving 2,3-bis-(2-pyridyl)-6-carboxydecylquinoxaline as a colorless semisolid which slowly crystallized (1.31 g, 96%).

The decyl, dodecyl, tetradecyl, hexadecyl and octadecyl esters can also be prepared using the same conditions as the octyl ester above.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various citations above to prior publications are incorporated herein by reference in their entireties.

What is claimed is:

1. A process for the preparation of a compound of the formula

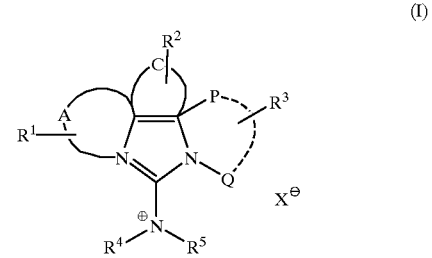

wherein A is a heteroaromatic ring, which may be optionally substituted by one or more $R^1$ substituents selected from the group consisting of aryl, heteroaryl, alkyl, hydroxy, halo, lower alkylamino, amino, nitro, cyano or carboxy substituents;

P or Q are optional substituents, each independently a substituent selected from the group consisting of aryl, heteroaryl, alkyl, hydroxy, halo, lower alkylamino, amino, nitro, or carboxy, or P and Q together are a heteroaromatic ring, said P and Q substituents independently or together which may optionally be substituted by one or more $R^3$ substituents selected from the group consisting of aryl, heteroaryl, alkyl, hydroxy, halo, lower alkylamino, amino, nitro, cyano or carboxy substituents;

C is an optional substituent which is an aromatic or heteroaromatic ring, which may optionally be substituted by one or more $R^2$ substituents selected from the group consisting of aryl, heteroaryl, alkyl, hydroxy, halo, lower alkylamino, amino, nitro, cyano or carboxy substituents; $R^4$ is hydrogen, a lower alkyl or aryl group, or together with $R^5$ and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group;

$R^5$ is a lower alkyl or aryl group, or together with $R^4$ and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group; and X is an anion, which comprises reaction of a compound with a first N—C—C—N moiety of the formula II

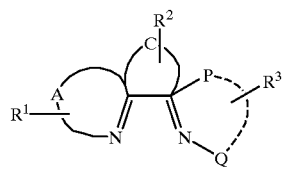

(II)

wherein A, C, P, Q, $R^1$, $R^2$ and $R^3$ are as hereinbefore defined, with a first N-substituted or N,N-disubstituted reactant selected from the group consisting of a thioformamide, a formamide acetal and a thioformamide acetal, wherein the N-substituents are $R^4$ and $R^5$, as hereinbefore defined, in a stoichiometric amount, in the presence of a halogenating agent selected from the group consisting of thionyl chloride, phosgene, and phosgene derivatives.

2. The process according to claim 1 wherein the phosgene derivative is selected from the group consisting of thiophosgene, oxalyl chloride, and oxalyl bromide.

3. The process according to claim 1 wherein said first N,N-disubstituted thioformamide is N,N-dimethylmethanethioamide.

4. The process of claim 1 wherein said first N,N-disubstituted formamide acetal is N,N-dimethyl formamide dimethyl acetal or N,N-dimethyl formamide dibenzyl acetal.

5. The process according to claim 1 wherein the reaction is conducted in a nonpolar aprotic solvent.

6. The process according to claim 1 wherein the reaction is conducted in a polar solvent.

7. The process according to claim 1 wherein the reaction is conducted under an inert atmosphere.

8. The process according to claim 1 wherein the reactant of Formula II contains at least one additional N—C—C—N moiety, which is reacted in a second step with an equivalent of a second N-substituted or N,N-disubstituted reactant selected from the group consisting of a formamide, a thioformamide, a formamide acetal or a thioformamide acetal, in the presence of a halogenating agent, to form a compound wherein said first N—C—C—N moiety is substituted by said first reactant and said at least one additional N—C—C—N moiety is substituted with said second reactant.

9. The process according to claim 8 wherein when said second reactant is a thioformamide, a formamide acetal or a thioformamide acetal, said halogenating agent is selected from the group consisting of thionyl chloride, phosgene and a phosgene derivative.

10. The process according to claim 8 wherein when said second reactant is a formamide said halogenating agent is selected from the group consisting of thionyl chloride, thionyl bromide, phosphorus oxychloride, phosphorus tribromide, phosphorus triiodide, phosgene, phosphorus thiochloride, thiophosgene, oxalyl chloride, oxalyl bromide, triphosgene and phosphorus oxychloride.

11. The process according to claim 1 wherein the reactant of Formula II contains a second N—C—C—N moiety, wherein both said first and said second N—C—C—N moieties are reacted in a single step with an N-substituted or N,N-disubstituted reactant selected from the group consisting of a thioformamide, a formamide acetal or a thioformamide acetal, in the presence of a halogenating agent, to form a compound wherein both said first N—C—C—N moiety and said second N—C—C—N moiety are substituted by said reactant.

12. The process according to claim 1 wherein the reactant of Formula II contains at least one additional N—C—C—N moiety, wherein only said first N—C—C—N moiety is reacted in a single step with an N-substituted or N,N-disubstituted reactant selected from the group consisting of a formamide, a thioformamide, a formamide acetal or a thioformamide acetal, in the presence of a halogenating agent, to form a compound wherein only one of said N—C—C—N moieties is substituted by said reactant.

13. The process of claim 12 wherein when said reactant is a thioformamide, a formamide acetal or a thioformamide acetal, said halogenating agent is selected from the group consisting of thionyl chloride, phosgene and a phosgene derivative, and when said reactant is a formamide, said halogenating agent is selected from the group consisting of thionyl chloride, thionyl bromide, phosphorus oxychloride, phosphorus tribromide, phosphorus triiodide, phosgene, phosphorus thiochloride, thiophosgene, oxalyl chloride, oxalyl bromide and phosphorus oxychloride.

14. The process of claim 8 or 12 wherein when the reactant of Formula II contains more than two N—C—C—N moieties, each of which is reacted successively and independently with a compound selected from the group consisting of an N-substituted or N,N-disubstituted reactant selected from the group consisting of a formamide, a thioformamide, a formamide acetal and a thioformamide acetal, wherein when said reactant is a thioformamide, a formamide acetal or a thioformamide acetal, said halogenating agent is selected from the group consisting of thionyl chloride, phosgene, and a phosgene derivative, and when said reactant is a formamide, said halogenating agent is selected from the group consisting of thionyl chloride, thionyl bromide, phosphorus oxychloride, phosphorus tribromide, phosphorus triiodide, phosgene, phosphorus thiochloride, thiophosgene, oxalyl chloride, oxalyl bromide and phosphorus oxychloride.

15. The process of claim 8 or 12 wherein the reactant of Formula II contains more than two N—C—C—N moieties and at least one of said N—C—C—N moieties is unreacted.

16. A process for the preparation of a compound of the formula

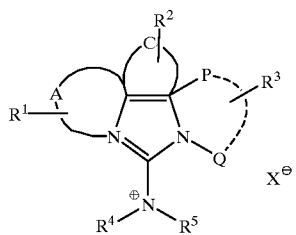

(I)

wherein A is a heteroaromatic ring, which may be optionally substituted by one or more $R^1$ substituents selected from the group consisting of aryl, heteroaryl, alkyl, hydroxy, halo, lower alkylamino, amino, nitro, cyano or carboxy substituents;

wherein P or Q are optional substituents, each independently a substituent selected from the group consisting of aryl, heteroaryl, alkyl, hydroxy, halo, lower alkylamino, amino, nitro, cyano or carboxy, or P and Q together are a heteroaromatic ring, said P and Q substituents independently or together which may optionally be substituted by one or more $R^3$ substituents selected from the group consisting of aryl, heteroaryl, alkyl, hydroxy, halo, lower alkylamino, amino, nitro, or carboxy substituents;

C is an optional substituent which is an aromatic or heteroaromatic ring, which may optionally be substituted by one or more $R^2$ substituents selected from the group consisting of aryl, heteroaryl, alkyl, hydroxy, halo, lower alkylamino, amino, nitro, or carboxy substituents;

$R^4$ is hydrogen, a lower alkyl or aryl group, or together with $R^5$ and the nitrogen atom to which it is attached, form a heterocyclic ring having from 5 to 7 members, which may optionally contain a sulfur, oxygen, silicon, selenium or an additional nitrogen atom, said ring optionally substituted with at least one alkyl group;

$R^5$ is a lower alkyl or aryl group, or together with $R^4$ and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group; and X is an anion, which comprises reaction of a compound of the formula II

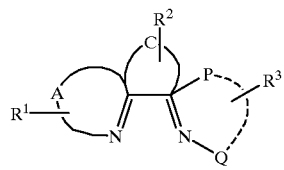

(II)

wherein A, C, P, Q, $R^1$, $R^2$ and $R^3$ are as hereinbefore defined, with an N-substituted or N,N-disubstituted formamide of the formula III

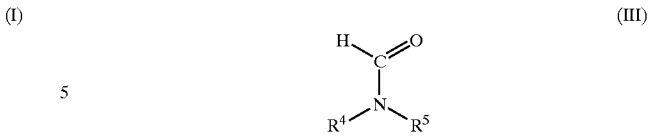

(III)

wherein $R^4$ and $R^5$ are as hereinbefore defined, in stoichiometric amounts, in the presence of a first halogenating agent;

and wherein said compound (II) has at least one additional N—C—C—N moiety which is reacted in a second step with a reactant selected from the group consisting of an N-substituted formamide, an N-substituted or N,N-disubstituted thioformamide, an N-substituted or N,N-disubstituted formamide acetal, and an N-substituted or N,N-disubstituted thioformamide acetal, in the presence of a second halogenating agent.

17. The process of claim 16 wherein when said reactant is a thioformamide, a formamide acetal or a thioformamide acetal, said halogenating agent is selected from the group consisting of thionyl chloride, phosgene, and a phosgene derivative, and when said reactant is a formamide, said halogenating agent is selected from the group consisting of thionyl chloride, thionyl bromide, phosphorus oxychloride, phosphorus tribromide, phosphorus triiodide, phosgene, phosphorus thiochloride, thiophosgene, oxalyl chloride, oxalyl bromide and phosphorus oxychloride.

18. The process of claim 16 wherein the reactant of Formula II contains more than two N—C—C—N moieties, each of which may be reacted successively and independently with a reactant selected from the group consisting of an N-substituted or N,N-distributed formamide, thioformamide, a formamide acetal and a thioformamide acetal, wherein when said reactant is a thioformamide, a formamide acetal or a thioformamide acetal, said halogenating agent is selected from the group consisting of thionyl chloride, phosgene, and a phosgene derivative, and when said reactant is a formamide, said halogenating agent is selected from the group consisting of thionyl chloride, thionyl bromide, phosphorus oxychloride, phosphorus tribromide, phosphorus triiodide, phosgene, phosphorus thiochloride, thiophosgene, oxalyl chloride, oxalyl bromide and phosphorus oxychloride.

19. The process of claim 11, wherein said reactant of Formula II contains more than two N—C—C—N moieties and all of said N—C—C—N moieties are substituted by said reactant.

20. A compound of the formula

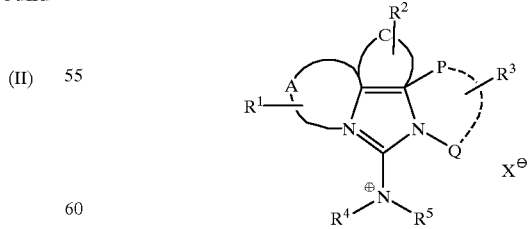

(I)

wherein A is a heteroaromatic ring, which may be optionally substituted by one or more $R^1$ substituents selected from the group consisting of aryl, heteroaryl, alkyl, hydroxy, halo, lower alkylamino, amino, nitro, cyano or carboxy substituents;

P or Q are optional substituents, each independently a substituent selected from the group consisting of aryl, heteroaryl, alkyl, hydroxy, halo, lower alkylamino, amino, nitro, or carboxy, or P and Q together are a heteroaromatic ring, said P and Q substituents independently or together which may optionally be substituted by one or more $R^3$ substituents selected from the group consisting of aryl, heteroaryl, alkyl, hydroxy, halo, lower alkylamino, amino, nitro, cyano or carboxy substituents;

C is an optional substituent which is an aromatic or heteroaromatic ring, which may optionally be substituted by one or more $R^2$ substituents selected from the group consisting of aryl, heteroaryl, alkyl, hydroxy, halo, lower alkylamino, amino, nitro, cyano or carboxy substituents;

$R^4$ is hydrogen, a lower alkyl or aryl group, or together with $R_5$ and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group;

$R^5$ is a lower alkyl or aryl group, or together with $R^4$ and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group; and X is an anion, and wherein at least one of said A, C, P or Q, $R^1$, $R^2$, or $R^3$ substitutents comprises an imidazolium group substituted with a group of the formula —$N(R^6)(R^7)$, wherein $R^6$ is hydrogen, a lower alkyl or aryl group, or together with $R^7$ and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group; $R^7$ is a lower alkyl or aryl group, or together with $R^6$ and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group, with the proviso that the combination of $R^6$ and $R^7$ is different from the combination of $R^4$ and $R^5$.

21. The compound according to claim 20 which contains at least one additional N—C—C—N moiety.

22. The compound of claim 21 wherein said at least one additional N—C—C—N moiety may be independently substituted with a —$N(R^4)(R^5)$ substituent to form a substituted imidazolium group.

23. The compound according to claim 20 which comprises from 3 to 15 additional N—C—C—N or substituted imidazolium groups.

* * * * *